(12) United States Patent
Templeton

(10) Patent No.: US 9,181,225 B2
(45) Date of Patent: Nov. 10, 2015

(54) TARGETED DELIVERY USING TISSUE-SPECIFIC PEPTIDOMIMETIC LIGANDS

(71) Applicant: GRADALIS, INC., Carrollton, TX (US)

(72) Inventor: Nancy Smyth Templeton, Houston, TX (US)

(73) Assignee: STRIKE BIO, INC., Dallas, TX (US)

( * ) Notice: Subject to any disclaimer, the term of this patent is extended or adjusted under 35 U.S.C. 154(b) by 153 days.

(21) Appl. No.: 13/664,288

(22) Filed: Oct. 30, 2012

(65) Prior Publication Data

US 2013/0129813 A1 May 23, 2013

Related U.S. Application Data

(63) Continuation of application No. 12/875,723, filed on Sep. 3, 2010, now Pat. No. 8,333,988.

(60) Provisional application No. 61/239,648, filed on Sep. 3, 2009.

(51) Int. Cl.
| | |
|---|---|
| *C07D 403/14* | (2006.01) |
| *A61K 31/711* | (2006.01) |
| *A61K 47/22* | (2006.01) |
| *A61K 47/48* | (2006.01) |
| *G01N 33/68* | (2006.01) |
| *C12Q 1/02* | (2006.01) |

(52) U.S. Cl.
CPC ............ *C07D 403/14* (2013.01); *A61K 31/711* (2013.01); *A61K 47/22* (2013.01); *A61K 47/48246* (2013.01); *C12Q 1/025* (2013.01); *G01N 33/6845* (2013.01)

(58) Field of Classification Search
None
See application file for complete search history.

(56) References Cited

U.S. PATENT DOCUMENTS

| | | | |
|---|---|---|---|
| 3,988,292 A * | 10/1976 | Moriga et al. | ............. 106/170.1 |
| 6,676,963 B1 | 1/2004 | Lanza et al. | |
| 7,037,520 B2 | 5/2006 | Templeton | |
| 8,333,988 B2 | 12/2012 | Templeton | |
| 2003/0180950 A1 | 9/2003 | Templeton | |
| 2009/0162425 A1 | 6/2009 | Divi et al. | |

FOREIGN PATENT DOCUMENTS

| | | |
|---|---|---|
| WO | 2009142892 A1 | 11/2009 |
| WO | 2011029028 A2 | 3/2011 |

OTHER PUBLICATIONS

Angell, Yu, et al., "A Combinatorial Method for Solution-Phase Synthesis of Labeled Bivalent â-Turn Mimics", j. am. chem. soc., 2008, 130:556-565.

Bruno, M., et al. "Long-Lasting Rescue of Age-Associated Deficits in Cognition and the CNS Cholinergic Phenotype by a Partial Agonist Peptidomimetic Ligand of TrkA", The Journal of Neuroscience, Sep. 15, 2004, 24(37):8009-8018.

Burgess, K., "Solid-Phase Syntheses of B-Turn Analogues to Mimic or Disrupt Protein—Protein Interactions", Acc. Chem. Res., 2001, 34:826-835.

Clonis, Y.D., "Affinity Chromatography Matures as Bioinformatic and Combinatorial Tools Develop", Journal of Chromatography, 2006, 1101, 1-24.

Fejzo, J., et al., "The Shapes Strategy: An NMR-Based Approach for Lead Generation in Drug Discovery", Research Paper 755, 1999, 6:10, 755-769.

Ferrara, N., et al., "Discovery and Development of Bevacizumab,An Anti-VEGF Antibody for Treating Cancer", Nature Reviews, Drug Discovery, May 2004, 3:391-400.

Gyongyossy-Issa, Maria, et al., "The Covalenr Coupling of Arg-Gly-Asp-Containing peptides to Liposomes: Purification and Biochemical Function of the Lipopeptide", XP-002356568, Archives of Biochemistry and Biophysics, May 1998, 353, 1, 101-108, Article No. BB980623.

Hashizume, H., et al., "Openings between Defective Endothelial Cells Explain Tumor Vessel Leakiness", American Journal of Pathology, Apr. 2000, 156(4), 1363-1380.

Isenberg, J., et al.,"Regulation of nitric oxide signaling by thrombospondin-1:implications for anti-angiogenic therapies", Nat Rev Cancer, Mar. 2009, 9(3): 182-194.

International Search Report, Korean Intellectual Property Office, Jun. 28, 2011, Gradalis, Inc. et al.

Jabbari, Esmaiel, "Targeted Delivery with Peptidomimetic Conjugated Self-Assembled Nanoparticles", Pharmaceutical Research, Mar. 2009, 26(3):612-630.

Lee, Che-Hsin, et al., "Systemic administration of attenuated Salmonella choleraesuis carrying thrombospondin-1 gene leads to tumor-specific transgene expression, delayed tumor growth and prolonged survival in the murine melanoma model", Cancer Gene Therapy, 2005, 12:175-184.

Lu, H., et al. "Enchanced Gene Expression in Breast Cancer Cells in Vitro and Tumors in Vivo", Molecular Therapy, Dec. 2002, 6(6):783-792.

Maliartchouk, S, et al, "A Designed Peptidomimetic Agonistic Ligand of TrkA Nerve Growth Factor Receptors", Molecular Pharmacology, 2007, 57:385-391.

Ramesh, R., et al., "Successful Treatment of primary and Disseminated Human Lung Cancers by Systemic Delivery of tumor Suppressor Genes Using an Improved Liposome Vector", Molecular Therapy, Mar. 2001, 3(3):337-350.

(Continued)

Primary Examiner — Samantha Shterengarts
(74) Attorney, Agent, or Firm — Edwin S. Flores; Chalker Flores, LLP

(57) ABSTRACT

Compositions and methods for tissue-specific targeted delivery of therapeutic agents through the use of tissue-specific peptidomimetic ligands are disclosed herein. The ligand comprises a composition of formula A-scaffold-A' and one or more hydrophobic anchors covalently linked to the scaffold. The A and A' compounds linked to the scaffold comprise monovalent peptidomimetic compounds wherein each monovalent peptidomimetic compound is selected from the group consisting of fragments IKs, GKs, IDs, GSs, GTs, VSs, TKs, KTs, ARs, KIs, KEs, AEs, GRs, YSs, IRs, and morpholino.

35 Claims, 25 Drawing Sheets

(56) References Cited

OTHER PUBLICATIONS

Reyes, S. et al., "Preferred Secondary Structures as a Possible Driving Force for Macrocyclization", 2000, Tetrahedron 56:9809-9818.
Park, Y-S, Tumor-Directed Targeting of Liposomes, XP-002628715, Bioscience Reports, Apr. 2002, 22(2):267-281.
Shi, Q, et al., "A combinatorial approach for targeted delivery using small molecules and reversible masking to bypass nonspecific uptake in vivo", Gene Therapy, 2010, 17:1085-1097.
Shuker, S.B., et al., "Discovering High-Affinity Ligands for Proteins: SAR by NMR", Science, New Series, Nov. 29, 1996, 274(5292): 1531-1534.
Soule, H. D., et al., "Human Breast Epithelial Cell Line, MCF-10 Isolation and Characterization of a Spontaneously Immortalized", Cancer Research, 1990, 50:6075-6086.
Tandle, A. et al., "Antiangiogenic gene therapy of cancer: recent developments", Journal of Translational Medicine, 2004, 2, 1-20.
Templeton, N.S., "Part One, Transductionally Targeted Vectors, Nonviral—Alternative Strategies for Targeted Delivery of Nucleic Acid-Liposome Complexes", Vector Targeting, 2002, 1-16.
Templeton, "Cationic Liposome-mediated Gene Delivery In vivo", Apr. 2002, XP-002490035, Bioscience Reports, 22(2): 283-295.
Templeton, "XP-002692210, The objective of this proposal is to define the in vivo effectiveness of a melanoma-targeted nanoparticle for systemic therapeutic delivery", 2011. SBIR Phase I Award.
Templeton, "Nonviral Delivery for Genomic Therapy of Cancer", World J. Surg., 2009, 33:685-697.
Thurston, G., et al., "Cationic Liposomes Target Angiogenic Endothelial Cells in Tumors and Chronic Inflammation in Mice", J. Clin. Invest., The American Society of Clinical Inestigation, Inc., Apr. 1998, 101(7):1401-1413.
Torchilin, V. P., et al., "TAT peptide on the surface of liposomes affords their efficient intracellular delivery even at low temperature and in the presence of metabolic inhibitors", PNAS, Jul. 17, 2001, 98(15):8786-8791.
Ulrich, A. S., "Biophysical Aspects of using Liposomes as Delivery vehicles", Bioscience Reports, Apr. 2002, 22(2):129-150.
Zhang, X, et al., "Adeno-Associated Virus-Mediated Antiangiogenic Gene Therapy with Thrombospondin-1 Type 1 Repeats and Endostatin", Clinical Cancer Research, 2007, 13:3968-3976.

\* cited by examiner

OCTADECYL LABELED HOMODIMERS

GENERAL STRUCTURE

FRAGMENT FOR COMPOUNDS KB991-KB1005:

| CODE | OLD | FRAGMENT A | FRAGMENT B | SEQUENCES A/B | M.W. | HPLC PURITY UV (%) | MASS SENT (mg) |
|---|---|---|---|---|---|---|---|
| KB991 | – | IKs | IKs | IK/IK | 989 | 90 | 5.0 |
| KB992 | – | GKs | GKs | GK/GK | 877 | 80 | 3.0 |
| KB993 | – | IDs | IDs | ID/ID | 991 | 88 | 3.0 |
| KB994 | – | GSs | GSs | GS/GS | 823 | 91 | 5.0 |
| KB995 | – | GTs | GTs | GT/GT | 851 | 92 | 3.0 |
| KB996 | – | VSs | VSs | VS/VS | 907 | 92 | 4.0 |
| KB997 | – | TKs | TKs | TK/TK | 965 | 65 | 3.0 |
| KB998 | – | KTs | KTs | KTKT | 993 | 70 | 5.0 |
| KB999 | – | ARs | ARs | AR/AR | 961 | 86 | 5.0 |
| KB1000 | – | KIs | KIs | KIKI | 989 | 90 | 4.0 |
| KB1001 | – | KEs | KEs | KE/KE | 1021 | 74 | 5.0 |
| KB1002 | – | AEs | AEs | AE/AE | 907 | 85 | 3.0 |
| KB1003 | – | GRs | GRs | GR/GR | 933 | 92 | 4.0 |
| KB1004 | – | YSs | YSs | YS/YS | 1035 | 88 | 5.0 |
| KB1005 | – | IRs | IRs | IR/IR | 1045 | 88 | 3.0 |

FIG. 5

| CODE | FRAGMENT A | FRAGMENT B | M.W. |
|---|---|---|---|
| KB1006 | IR | MORPHOLINE | 995.38 |
| KB1007 | IR | KT | 1232.68 |
| KB1008 | IR | TK | 1218.66 |
| KB1009 | IR | KI | 1230.71 |
| KB1010 | IR | KE | 1246.67 |
| KB1011 | IR | ID | 1231.65 |
| KB1012 | IR | IK | 1230.71 |
| KB1013 | IR | GS | 1147.53 |
| KB1014 | IR | GT | 1161.56 |
| KB1015 | IR | VS | 1189.61 |
| KB1016 | IR | AE | 1189.57 |
| KB1017 | IR | GK | 1174.6 |
| KB1018 | IR | AR | 1216.64 |
| KB1019 | IR | GR | 1202.62 |
| KB1020 | IR | YS | 1253.66 |
| KB1021 | YS | MORPHOLINE | 990.32 |
| KB1022 | YS | KT | 1227.62 |
| KB1023 | YS | TK | 1213.6 |
| KB1024 | YS | KI | 1225.65 |
| KB1025 | YS | KE | 1241.61 |
| KB1026 | YS | ID | 1226.59 |
| KB1027 | YS | IK | 1225.65 |
| KB1028 | YS | GS | 1142.47 |
| KB1029 | YS | GT | 1156.5 |
| KB1030 | YS | VS | 1184.55 |
| KB1031 | YS | AE | 1184.51 |
| KB1032 | YS | GK | 1169.54 |
| KB1033 | YS | AR | 1211.58 |
| KB1034 | YS | GR | 1197.56 |
| KB1035 | GR | MORPHOLINE | 939.28 |
| KB1036 | GR | KT | 1176.58 |
| KB1037 | GR | TK | 1162.56 |
| KB1038 | GR | KI | 1174.61 |
| KB1039 | GR | KE | 1190.57 |
| KB1040 | GR | ID | 1175.55 |
| KB1041 | GR | IK | 1174.61 |
| KB1042 | GR | GS | 1091.43 |
| KB1043 | GR | GT | 1105.46 |
| KB1044 | GR | VS | 1133.51 |

MORPHOLINE

| | | | |
|---|---|---|---|
| KB1045 | GR | AE | 1133.47 |
| KB1046 | GR | GK | 1118.5 |
| KB1047 | GR | AR | 1160.54 |
| KB1048 | AR | MORPHOLINE | 953.3 |
| KB1049 | AR | KT | 1190.6 |
| KB1050 | AR | TK | 1176.58 |
| KB1051 | AR | KI | 1188.63 |
| KB1052 | AR | KE | 1204.59 |
| KB1053 | AR | ID | 1189.57 |
| KB1054 | AR | IK | 1188.63 |
| KB1055 | AR | GS | 1105.45 |
| KB1056 | AR | GT | 1119.48 |
| KB1057 | AR | VS | 1147.53 |
| KB1058 | AR | AE | 1147.49 |
| KB1059 | AR | GK | 1132.52 |
| KB1060 | GK | MORPHOLINE | 911.26 |
| KB1061 | GK | KT | 1148.56 |
| KB1062 | GK | TK | 1134.54 |
| KB1063 | GK | KI | 1146.59 |
| KB1064 | GK | KE | 1162.55 |
| KB1065 | GK | ID | 1147.53 |
| KB1066 | GK | IK | 1146.59 |
| KB1067 | GK | GS | 1063.41 |
| KB1068 | GK | GT | 1077.44 |
| KB1069 | GK | VS | 1105.49 |
| KB1070 | GK | AE | 1105.45 |
| KB1071 | AE | MORPHOLINE | 926.23 |
| KB1072 | AE | KT | 1163.53 |
| KB1073 | AE | TK | 1149.51 |
| KB1074 | AE | KI | 1161.56 |
| KB1075 | AE | KE | 1177.52 |
| KB1076 | AE | ID | 1162.5 |
| KN1077 | AE | IK | 1161.56 |
| KN1078 | AE | GS | 1078.38 |
| KB1079 | AE | GT | 1092.41 |
| KB1080 | AE | VS | 1120.46 |
| KB1081 | VS | MORPHOLINE | 926.27 |
| KB1082 | VS | KT | 1163.57 |
| KB1083 | VS | TK | 1149.55 |
| KB1084 | VS | KI | 1161.6 |
| KB1085 | VS | KE | 1177.56 |
| KB1086 | VS | ID | 1162.54 |
| KB1087 | VS | IK | 1161.6 |
| KB1088 | VS | GS | 1078.42 |
| KN1089 | VS | GT | 1092.45 |

FIG. 7b

| | | | |
|---|---|---|---|
| KB1090 | GT | MORPHOLINE | 898.22 |
| KB1091 | GT | KT | 1135.52 |
| KB1092 | GT | TK | 1121.5 |
| KB1093 | GT | KI | 1133.55 |
| KB1094 | GT | KE | 1149.51 |
| KB1095 | GT | ID | 1134.49 |
| KB1096 | GT | IK | 1133.55 |
| KB1097 | GT | GS | 1050.37 |
| KB1098 | GS | MORPHOLINE | 884.19 |
| KB1099 | GS | KT | 1121.49 |
| KB1100 | GS | TK | 1107.47 |
| KB1101 | GS | KI | 1119.52 |
| KB1102 | GS | KE | 1135.48 |
| KB1103 | GS | ID | 1120.46 |
| KB1104 | GS | IK | 1119.52 |
| KB1105 | IK | MORPHOLINE | 967.37 |
| KB1106 | IK | KT | 1204.67 |
| KB1107 | IK | TK | 1190.65 |
| KB1108 | IK | KI | 1202.7 |
| KB1109 | IK | KE | 1218.66 |
| KB1110 | IK | ID | 1203.64 |
| KB1111 | ID | MORPHOLINE | 968.31 |
| KB1112 | ID | KT | 1205.61 |
| KB1113 | ID | TK | 1191.59 |
| KB1114 | ID | KI | 1203.64 |
| KB1115 | ID | KE | 1219.6 |
| KB1116 | KE | MORPHOLINE | 983.33 |
| KB1117 | KE | KT | 1220.63 |
| KB1118 | KE | TK | 1206.61 |
| KB1119 | KE | KI | 1218.66 |
| KB1120 | KI | MORPHOLINE | 967.37 |
| KB1121 | KI | KT | 1204.67 |
| KB1122 | KI | TK | 1190.65 |
| KB1123 | TK | MORPHOLINE | 955.32 |
| KB1124 | TK | KT | 1192.62 |
| KB1125 | KT | MORPHOLINE | 969.34 |
| KB1126 | IR | IR | 1258.72 |
| KB1127 | YS | YS | 1248.6 |
| KB1128 | GR | GR | 1146.52 |
| KB1129 | AR | AR | 1174.56 |
| KB1130 | GK | GK | 1090.48 |
| KB1131 | AE | AE | 1120.42 |
| KB1132 | VS | VS | 1120.5 |
| KB1133 | GT | GT | 1064.4 |
| KB1134 | GS | GS | 1036.34 |

FIG. 7c

| KB1135 | IK | IK | 1202.7 |
| KB1136 | ID | ID | 1204.58 |
| KB1137 | KE | KE | 1234.62 |
| KB1138 | KI | KI | 1202.7 |
| KB1139 | TK | TK | 1178.6 |
| KB1140 | KT | KT | 1206.64 |
FIG. 7d
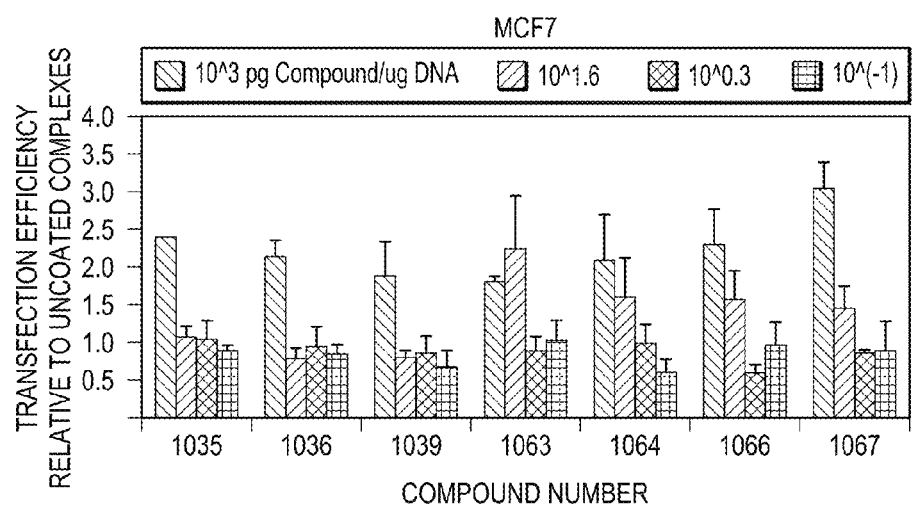
FIG. 8
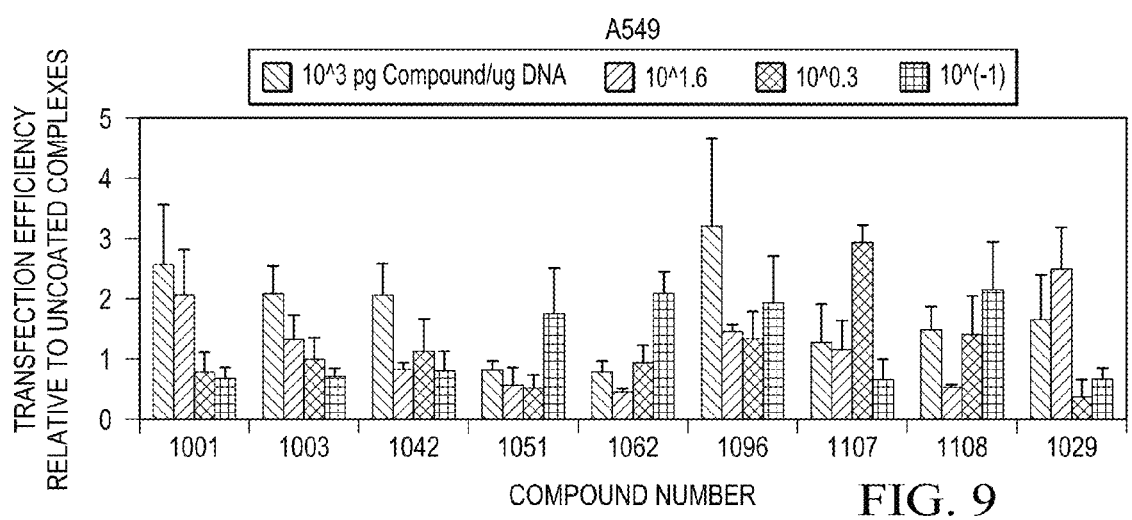
FIG. 9

TARGETED DELIVERY USING TISSUE-SPECIFIC PEPTIDOMIMETIC LIGANDS

CROSS-REFERENCE TO RELATED APPLICATIONS

This application claims priority to U.S. Provisional Application Ser. No. 61/239,648, filed Sep. 3, 2009, and is a Continuation of U.S. Ser. No. 12/875,723, filed on Sep. 3, 2010, the entire contents of which are incorporated herein by reference.

STATEMENT OF FEDERALLY FUNDED RESEARCH

This invention was made with U.S. Government support from the National Institutes of Health (MH070040, GM076261), and the Intramural Research Program of the NIH, NCI, Center for Cancer Research. The government has certain rights in this invention.

TECHNICAL FIELD OF THE INVENTION

The present invention relates in general to the field of disease treatment and diagnostics, and more particularly, to the development of novel compositions and methods to deliver agents to a specific target tissue.

BACKGROUND OF THE INVENTION

Without limiting the scope of the invention, its background is described in connection with the delivery to specific target tissues.

Intravenous injection of therapeutics for the treatment of cancer is considered the ultimate therapeutic because all tumors and their metastases are sustained by blood vessels. These tumor vascular beds are leaky enough to allow liposomes direct access to tumor cells. Anti-angiogenic drugs or gene therapeutics delivered to the tumor vasculature could be used to block the blood supply to tumors, thereby causing tumor regression.

Targeted delivery is essential for greatest efficacy and reduced toxicity. The major constraints on the broad therapeutic applications of most liposomal delivery systems are their poor transfection efficiencies in vivo, accumulation in the lungs after intravenous delivery, aggregation, clearance after systemic delivery (e.g., by Kupffer cells), inability to deliver the bulk of injected liposomal complexes to the target cells and organs, and other issues. Targeted delivery for treatment of cancer is further complicated by the lack of known cell surface receptors to use for efficient targeting.

SUMMARY OF THE INVENTION

The present invention includes a targeting ligand for tissue-specific targeted delivery of therapeutic agents. The ligand comprises a composition of formula A-scaffold-A' and one or more hydrophobic anchors covalently linked to the scaffold. The A and A' compounds linked to the scaffold comprise monovalent peptidomimetic compounds wherein each monovalent peptidomimetic compound is selected from the group consisting of fragments IKs, GKs, IDs, GSs, GTs, VSs, TKs, KTs, ARs, KIs, KEs, AEs, GRs, YSs, IRs, and morpholino. Compounds A and A' may be the identical. The scaffold may comprise a reactive dichlorotriazine group. In one embodiment, one or more of the hydrophobic anchors comprise a hydrocarbon moiety. In one example, the hydrocarbon moiety may be an ocotadecyl group. The targeted ligand may further include one or more linkers, cleavable or non-cleavable, functionally interposed between the scaffold and the hydrophobic anchors.

The present invention also provides a method of synthesizing a small molecule complex for targeted delivery of therapeutic agents. The method includes coupling covalently two or more monovalent peptidomimetic compounds to a scaffold, wherein each monovalent peptidomimetic compound is selected from the group consisting of fragments IKs, GKs, IDs, GSs, GTs, VSs, TKs, KTs, ARs, KIs, KEs, AEs, GRs, YSs, IRs, and morpholino; and, coupling covalently one or more hydrophobic anchors to the scaffold. Compounds A and A' may be the identical. The scaffold may comprise a reactive dichlorotriazine group. In one embodiment, one or more of the hydrophobic anchors comprise a hydrocarbon moiety. In one example, the hydrocarbon moiety may be an ocotadecyl group. The targeted ligand may further include one or more linkers, cleavable or non-cleavable, functionally interposed between the scaffold and the hydrophobic anchors.

The present invention also includes a ligand-functionalized delivery system comprising a therapeutic agent carrier, and a targeting ligand for tissue-specific target delivery of therapeutic agents. In one embodiment, the therapeutic agent carrier is a liposome. In one example, the targeting ligand is non-covalently anchored to the exterior surface of the external lipid bilayer of a cationic liposome having an internal lipid bilayer and an external lipid bilayer through one or more hydrophobic anchors.

Another embodiment of the present invention includes a method of delivering a payload to a target tissue. The methods includes the steps of synthesizing a targeting ligand for tissue-specific target delivery of therapeutic agents; incorporating the targeting ligand into a lipid bilayer such as a cell membrane or a subcellular membrane, or a multlilamellar or bilamellar vessicle or more specifically a bilamellar liposome that encapsulates a therapeutic agent; coating the liposome with a targeting ligand; combining the targeted liposome complex with a reversible masking reagent; and, administering a therapeutically effective amount of the masked targeted liposome complex to a patient. In one embodiment, the liposome may be a bilamellar invaginated vesicle ("BIV"). Small neutral lipids with molecular weight of about 500 Da or lower may be used as reversible masking agents. The target tissues may include human pancreatic cancer, human breast cancer, human non-small cell lung carcinoma, human non-small cell lung carcinoma vascular endothelium, a melanoma, or human pancreatic cancer vascular endothelium. Examples of targeting ligands include at least one of compounds KB995, KB1001, KB1003, KB1005, KB1012, KB1023, KB1029, KB1035, KB1036, KB1039, KB1042, KB1051, KB1061, KB1062, KB1063, KB1064, KB1066, KB1067, KB1096, KB1107, KB1108, or KB1109. In one aspect, the target tissue is a melanoma and the targeting ligand is compound is at least one of KB1037, KB1109 and KB1123.

In another embodiment, the present invention includes a method of isolating a peptidomimetic compound for binding to a target tissue comprising the steps of: preparing a composition of formula: A-scaffold-A', wherein A and A' comprise monovalent peptidomimetic compounds, wherein each monovalent peptidomimetic compound is selected from the group consisting of fragments IKs, GKs, IDs, GSs, GTs, VSs, TKs, KTs, ARs, KIs, KEs, AEs, GRs, YSs, IRs, and morpholino; and one or more hydrophobic anchors covalently linked to the scaffold; contacting a target tissue with the peptidomimetic compounds; isolating those peptidomimetic compounds that binding specifically to the target tissue; and characterizing the formula of the composition that bound specifically to the target tissue. The target tissues may include human pancreatic cancer, human breast cancer, human non-small cell lung carcinoma, human non-small cell lung carcinoma vascular endothelium, a human melanoma, or human pancreatic cancer vascular endothelium. In one aspect, the method includes a high throughput assay to screen patient cells directly post-dissociation. In one aspect, the peptidomimetic compound library is labeled with, e.g., a europium or a terbium cryptate in place of a hydrophobic tail. The dissociated patient cells, tumor versus normal, are screened directly using time resolved fluorometry.

In one embodiment, the present invention includes a method of screening for a peptidomimetic compound that binds to a target tissue or cell comprising the steps of: preparing a peptidomimetic library of compositions of formula: A-scaffold-A', wherein A and A' comprise peptidomimetic compounds, wherein each monovalent peptidomimetic compound is selected from the group consisting of fragments IKs, GKs, IDs, GSs, GTs, VSs, TKs, KTs, ARs, KIs, KEs, AEs, GRs, YSs, IRs, and morpholino; attaching one or more bi-lipid layer anchors covalently to the peptidomimetic compounds; mixing the peptidomimetic compounds with lipids to form liposomes; contacting a target tissue with the peptidomimetic compounds; isolating those peptidomimetic compounds that binding specifically to the target tissue; and characterizing the formula of the composition that bound specifically to the target tissue.

Yet another embodiment is a method of screening for a peptidomimetic compound that binds to a target tissue or cell comprising the steps of: preparing a peptidomimetic library of compositions of formula: A-scaffold-A', wherein A and A' comprise peptidomimetic compounds, wherein each monovalent peptidomimetic compound is selected from the group consisting of fragments IKs, GKs, IDs, GSs, GTs, VSs, TKs, KTs, ARs, KIs, KEs, AEs, GRs, YSs, IRs, and morpholino; attaching one or more bi-lipid layer anchors covalently to the peptidomimetic compounds; mixing the peptidomimetic compounds with lipids to form liposomes, wherein the liposomes further comprise a nucleic acid for delivery to a cell; contacting a target tissue with the peptidomimetic compounds; isolating those peptidomimetic compounds that binding specifically to the target tissue; and characterizing the formula of the composition that bound specifically to the target tissue. In one aspect, the target tissue is defined further as cells in tissue culture. In another aspect, the target tissue is defined further as cells in tissue culture and the cells are selected based on the effect of the nucleic acid on the cells. In yet another aspect, the target tissue is defined further as cells in tissue culture, wherein the nucleic acid is a selective marker for negative or positive selection, expresses a selective marker for positive or negative selection, or expresses a detectable marker.

BRIEF DESCRIPTION OF THE DRAWINGS

For a more complete understanding of the features and advantages of the present invention, reference is now made to the detailed description of the invention along with the accompanying figures and in which:

FIG. 5 summarizes the combinations of the binding portions of the present invention (A and/or A').

FIGS. 7a to 7d show the optimization of the portion of the binding portions of the present invention (A=Frag. A and/or A'=Frag. B).

FIG. 8 is a graph that shows the transfection efficiency of the listed compounds against MCF7 cells.

FIG. 9 is a graph that shows the transfection efficiency of the listed compounds against A549 cells.

DETAILED DESCRIPTION OF THE INVENTION

Figure 1:
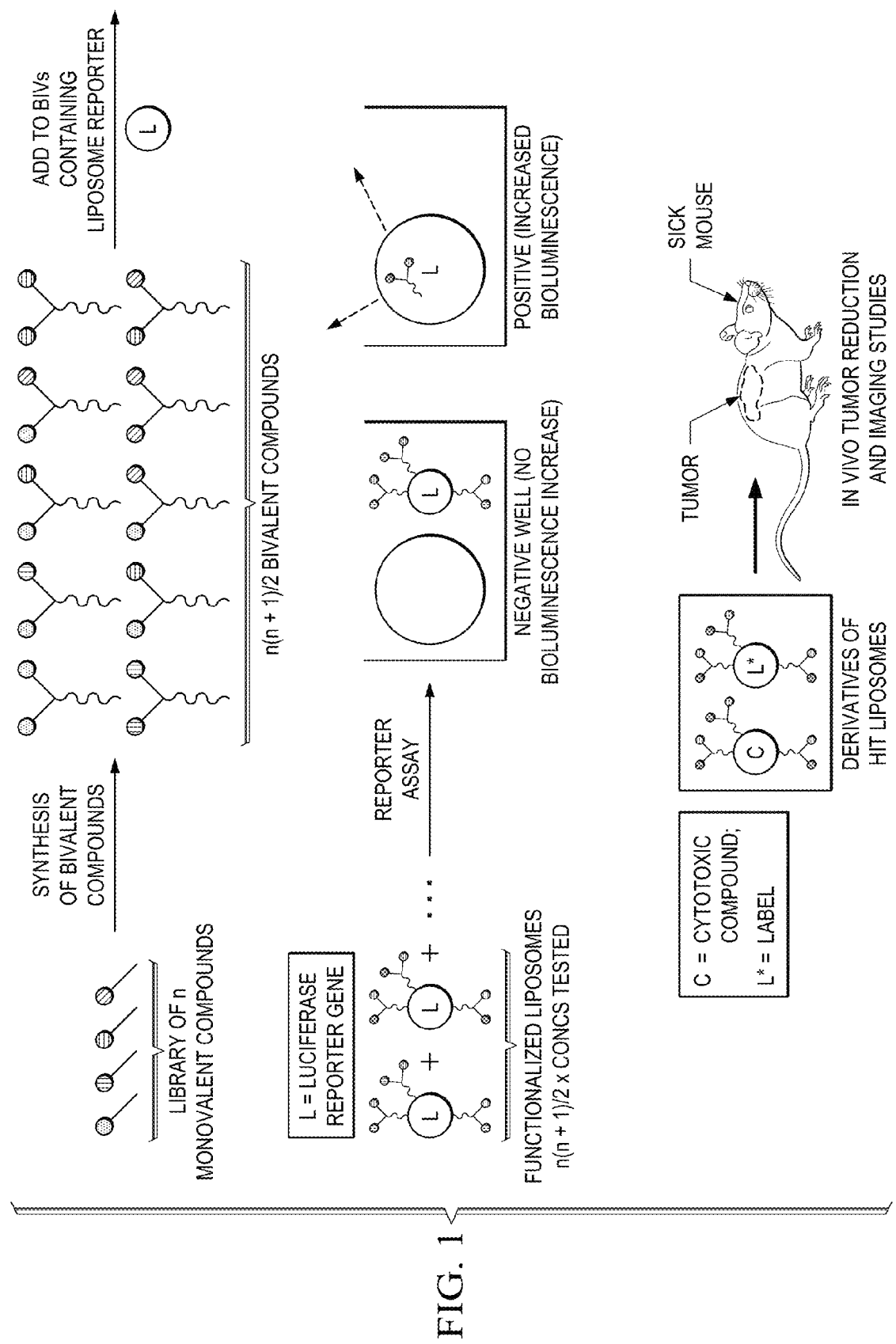
FIG. 1 is diagram of the general schema for identifying the compounds.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Small peptides multimerized on the surface of liposomes can generate immune responses after repeated injections, particularly systemically, and peptides can preclude penetration and delivery across the interstitial pressure gradient of tumors. Other larger ligands including antibodies, antibody fragments, proteins, partial proteins, etc. are far more refractory than using small peptides for targeted delivery on the surface of liposomes. What is needed are small non-immunogenic molecules that can be placed on the surface of delivery systems, such as liposomes, to target them selectively to target tissues.

A peptidomimetic is a molecule that mimics the biological activity of a peptide but is no longer peptidic in chemical nature. The term peptidomimetic describes, in general, a molecule that no longer contains any peptide bonds (that is, amide bonds between amino acids).

As used herein, the term "peptidomimetic" refers to molecules that are no longer completely peptidic in nature, such as pseudopeptides, semi-peptides, and peptoids. Whether completely or partially non-peptide, peptidomimetics according to this invention provide a spatial arrangement of reactive chemical moieties that closely resembles the three-dimensional arrangement of secondary structure motifs found at hotspots in protein-ligand interactions, e.g. bivalent beta-turn mimics designed to have an affinity for cell surface receptors.

Targeted delivery of liposome payloads is essential for greatest efficacy and reduced toxicity. Generally, the present invention provides ligands that mediate delivery of therapeutics into target cells more efficiently than existing methodologies. The present invention also provides methods for synthesizing the targeting ligands and methods for effective delivery of therapeutics into target cells using the ligands. The fact that these targeting ligands are small molecules allows for repeated injections indefinitely without generating immune responses. The technology created improves targeted delivery of therapeutics and imaging agents selectively to diseased cells. This technology can be applied to numerous diseases and disorders including different types of cancer. A small molecule library was created and screened for specificity to a number of human cancer tissues, such as pancreatic cancer, breast cancer, non-small cell lung carcinoma (NSCLC), pancreatic cancer vascular endothelium, a melanoma or NSCLC cancer vascular endothelium.

The major constraints on the broad therapeutic applications of most liposomal delivery systems are their poor transfection efficiencies in vivo, accumulation in the lungs after intravenous delivery, aggregation, clearance (e.g., by Kupffer cells) after systemic delivery, inability to deliver the bulk of injected liposomal complexes to the target cells and organs, and other issues. Bilamellar invaginated vesicles ("BIVs") overcome these constraints [1,2]. The development of BIVs as a therapeutic tool is hindered by the absence of non-immunogenic ligands that can be placed on the surface of BIV-complexes to direct them to target cells. Small peptides that are multimerized on the surface of liposomes can generate immune responses after repeated injections, particularly systemically, and peptides can preclude penetration and delivery across the interstitial pressure gradient of tumors. Other larger ligands including antibodies, antibody fragments, proteins, partial proteins, etc. are far more refractory than using small peptides for targeted delivery on the surface of liposomes. The present invention provides non-immunogenic targeting ligands to deliver BIVs and other therapeutic agent carriers selectively to cancer tissues.

The present invention provides targeting complexes that are unique insofar as they penetrate tight barriers including the interstitial pressure gradient of solid tumors [3], thus BIV complexes achieve targeted delivery to tumor cells directly. This therapeutic approach is not limited to delivery to tumor cell vasculature to achieve efficacy in the treatment of cancers. Other investigators have also shown that tumor vascular beds are leaky enough to allow liposomes direct access to tumor cells [4-6]. Furthermore, recent publications have reported that tumor cells, which are accessible to the circulation undergo a differentiation process called "vasculogenic mimicry" wherein they express vascular markers on their surface rather than tumor cell markers [7,8]. The small molecule targeting ligands provided in the present invention can deliver anti-angiogenic drugs or gene therapeutics to the tumor vasculature to block the blood supply to tumors, thereby causing tumor regression.

Targeted delivery for treatment of cancer is further complicated by the lack of known cell surface receptors to use for efficient targeting. Optimal ligands should be small (about 500 Da or less, e.g., drugs and small molecules), and should have high affinity and internalization into unique receptors found exclusively on the target cells. Prior to our invention, no optimal small molecule ligands had been identified that selectively target cell surface receptors on specific cancer cells and cancer subtypes. The present invention includes a library of small molecule targeting ligands to search for better cell surface receptors to use for targeted delivery. This targeting strategy does not require knowing the function and identity of the best unique receptors.

FIG. 1 shows the essential parts of the small molecule library design. "Monovalent" small molecules that potentially mimic protein hot-spots are used to form a larger library of "bivalent ligands", each equipped with a hydrocarbon anchor (e.g., a hydrophobic tail). The bivalent ligands are particularly appropriate for binding cell surface receptors, and will resemble secondary structure motifs found at hot-spots in protein-ligand interactions. The hydrocarbon anchor allows the monovalent and bivalent ligands to be anchored into liposomal complexes, simply by mixing and incubation overnight. In one embodiment of the invention, the liposomes used are BIVs [1]. In another example, the peptidomimetic compound library is labeled with, e.g., a europium or a terbium cryptate tail in place of the hydrophobic tail. The library can then be screened directly using time resolved fluorometry.

Small Molecules Designed To Bind Cell Surface Receptors: Many protein-protein interactions at cell surfaces involve dimeric or oligomeric ligands docking with dimeric or oligomeric receptors. It is difficult to design small molecules that mimic the ligands involved in these interactions. The approach used by Burgess and co-workers is to make small molecules that have side chains exactly corresponding to the amino acids found in proteins, on organic frameworks which closely match proteins secondary structures found at hot-spots in protein-protein interactions. These are then joined together to form bivalent molecules, which could potentially bind two sites on a receptor considerably increasing the free energy loss on binding, e.g., "semi-peptidic" beta-turn analogs [9-17]. Significantly, these compounds can incorporate any amino acid side chains, so they can be designed to mimic turns at any hot spot that involves that motif. They tend to match well with beta-turn conformations, and are active against some protein-protein interaction targets that have turn hot-spots [18-25]. Bivalent derivatives of these compounds can have dramatically enhanced binding affinities. These bivalent molecules are prepared via the chemistry highlighted in Scheme 1 that allows selective coupling of two monovalent, unprotected, peptidomimetics just by mixing them in the presence of a triazine linker. The key feature of this route is that two functionalized monovalent molecules can be combined to give heterodimers selectively in solution, and only potassium carbonate is required to affect the coupling. Unlike most combinatorial syntheses, no protecting groups are involved in the last steps of this approach, so the final product does not have to be purified from protecting group residues and added scavenger materials.

Figure 2:
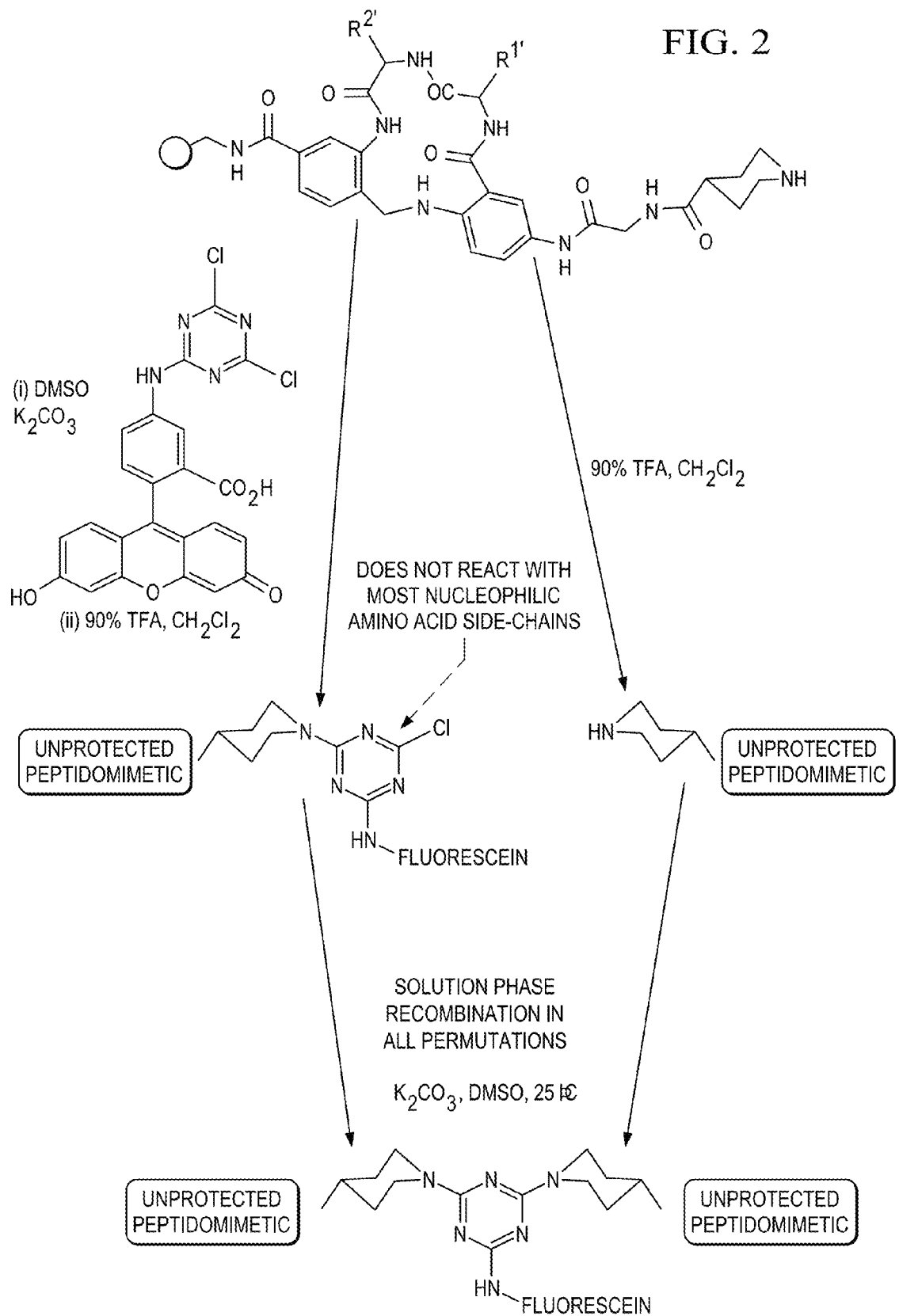
FIG. 2 shows preparation of dimers via selective reactions of a piperidine with a substituted fluorescein.
Figure 3:
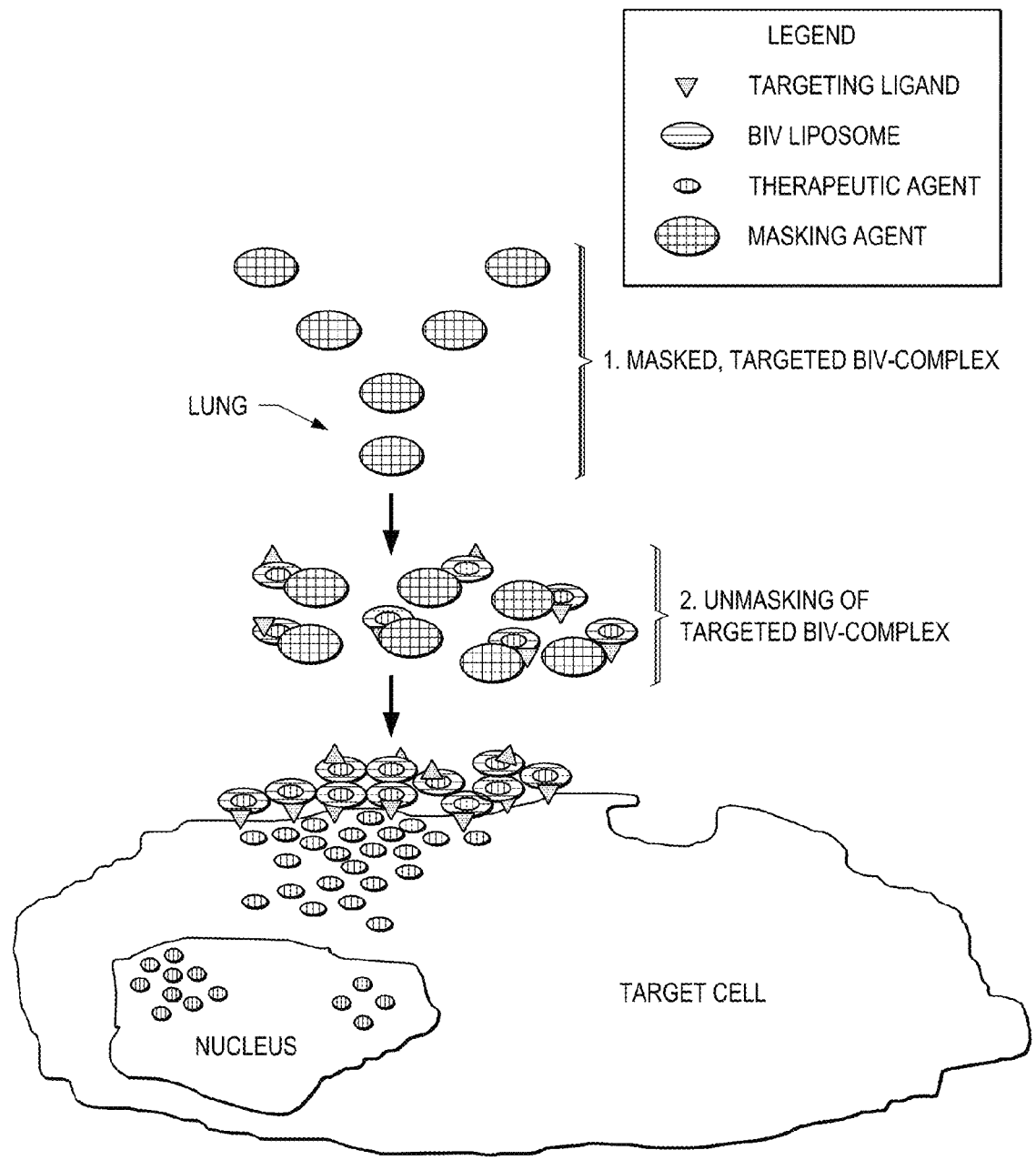
FIG. 3 shows the optimization of the optimized targeting strategy for delivery of greater than 90% of iv injected BIV complexes exclusively into the target cell.

Synthesis of an Exploratory Library: An exploratory library of 150 compounds was prepared, 15 homodimer and 135 heterodimer bivalent small molecules, for our studies using the methods outlined. FIG. 2 shows the synthetic scheme for the dimers via selective reactions of a piperidine with a substituted fluorescein. Their structures are listed in FIGS. 4, 5, 6, and 7a to 7d. The molecular weights listed include that of the hydrocarbon tail plus two small molecules. These compounds are different than other compound libraries that have been prepared before insofar as they have polar "warhead" functionalities (mimics A and B) and the hydrophobic tails.

Figure 11:
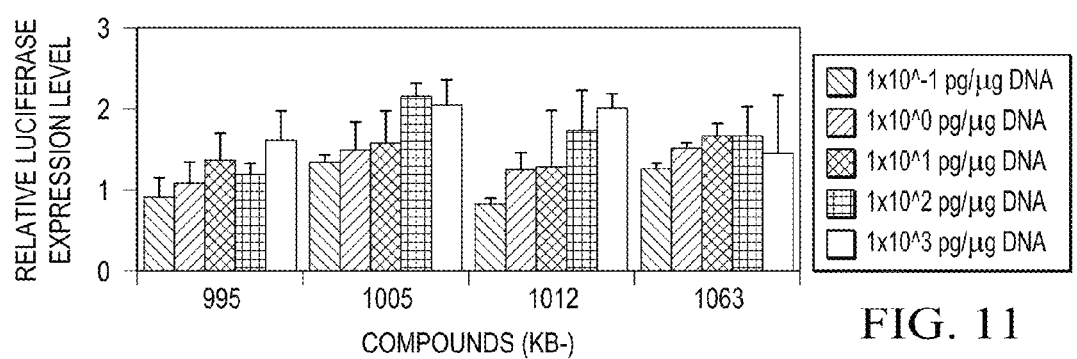
FIG. 11 is a graph that shows the relative luciferase expression in Panc1 cells using the listed compounds in a coated liposome delivery system.
Figure 12:
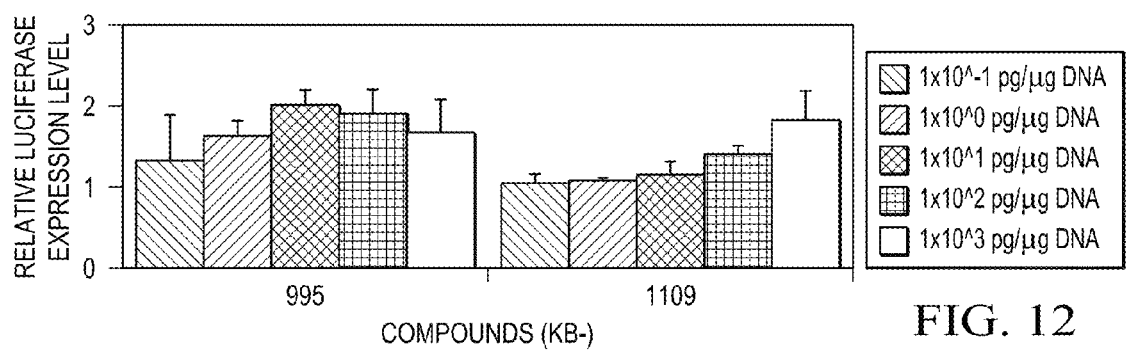
FIG. 12 is a graph that shows the relative luciferase expression in Mia PaCa2 cells using the listed compounds in a coated liposome delivery system.
Figure 13:
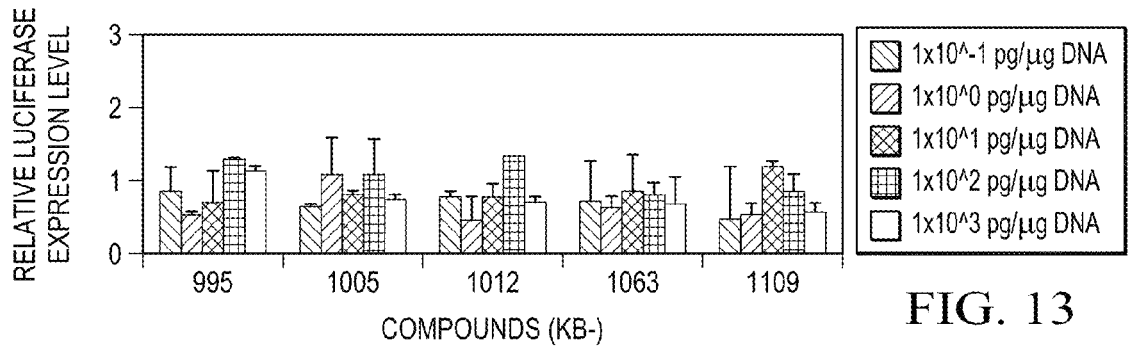
FIG. 13 is a graph that shows the relative luciferase expression in HPDE cells using the listed compounds in a coated liposome delivery system.
Figure 14:
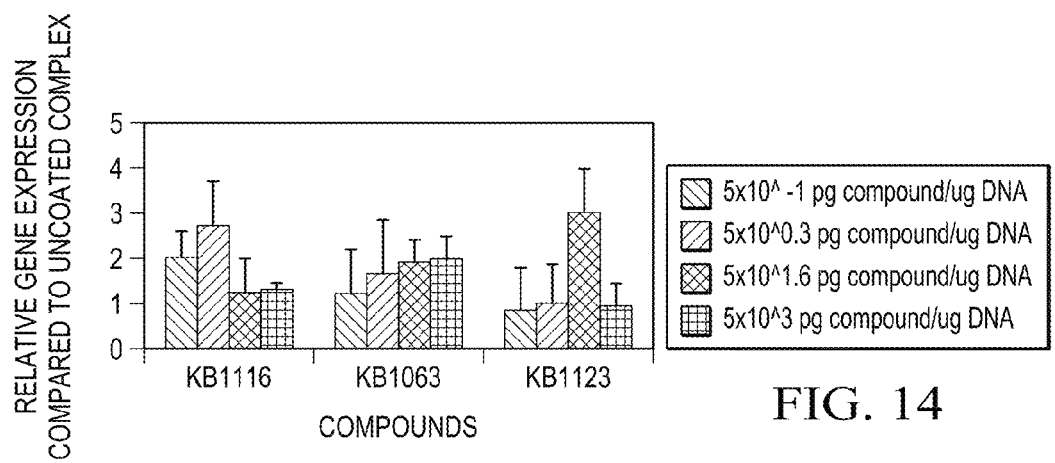
FIG. 14 shows the transfection enhancement in a co-culture of HUVEC and HI299 cells with the listed compounds.
Figure 15:
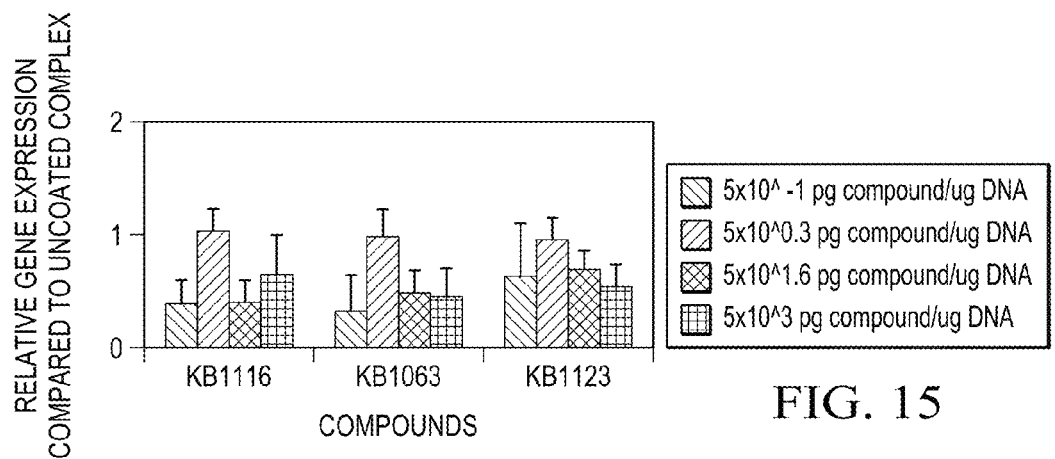
FIG. 15 shows the shows the transfection results in a culture of HI299 cells alone with the listed compounds, no enhancement was noted.
Figure 16:
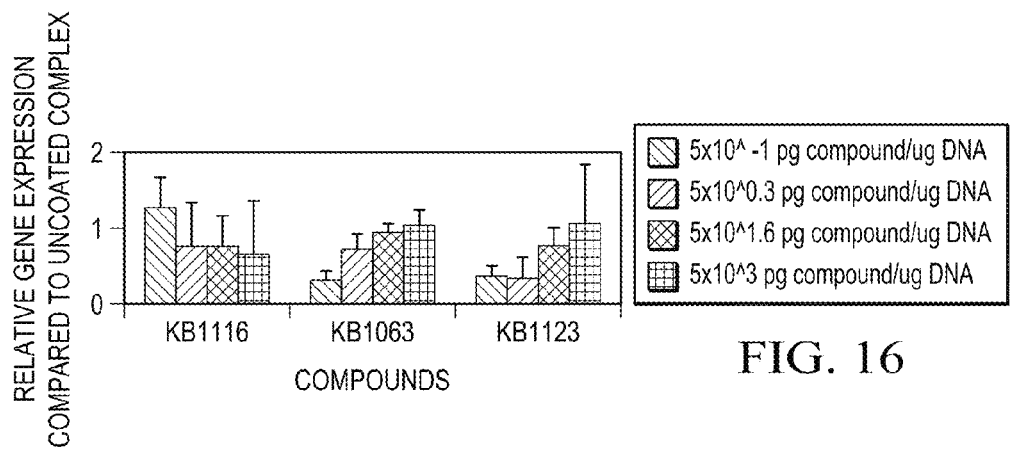
FIG. 16 shows the transfection enhancement in a culture of HUVEC cells alone with the listed compounds, no enhancement was noted.

In Vitro Delivery and High Throuphput Assays: Highly sensitive and accurate detection systems are required for successful high throughput screens. A high throughput assay was used to identify monovalent or bivalent compounds attached to the surface of BIV complexes that internalize into cancer cells or human tumor endothelium more efficiently than non-targeted BIV complexes. Bivalent ligands coated on BIV complexes are selected for their ability to bind to and internalize the encapsulated reagents across the cell membrane. The screening method is far more direct and powerful than the best contemporary methods featuring phage display because those simply provide a read-out for cell surface binding and generate numerous false positives. The present invention enables delivery of ligand-functionalized BIVs via unidentified cancer cell surface receptors.

Reversible Masking of BIVs: Reversible masking initially provides temporary shielding of positive charge of BIV complexes during delivery in order to bypass non-target organs and then provides re-exposed charge at the target cell surface to allow fusogenic entry. Therefore, the mask that provides shielding of charge dissociates from the BIV complexes and is, therefore, reversible. One of the reasons the BIV delivery system is uniquely efficient is because the complexes deliver therapeutics into cells by fusion with the cell membrane and avoid the endocytic pathway. The present invention avoids uptake in the lungs and other non-specific target organs using "shielding/deshielding compounds" that can be added to the complexes used for targeted delivery just prior to injection or administration in vivo (Templeton, N. S. U.S. Pat. No. 7,037,520 B2 issued May 2, 2006, relevant portions incorporated herein by reference). The strategy to bypass non-specific transfection is called "reversible masking" and uses neutral, small molecular weight lipids (about 500 MW and lower), e.g., n-dodecyl-beta-D-maltopyranoside. These lipids are small and not charged, so they are loosely associated with the surface of BIV complexes and are removed by sheer force in the bloodstream by the time they reach the target cell.

Another reason the BIV ligand-coated, reversibly-masked complexes are efficiently delivered is that they re-expose the overall positive charge of the complexes as they approach the target cells. By removing the "mask" at the target cell, adequate overall positive charge on the surface of complexes is preserved to enter the target cell by a fusogenic pathway. Thus, an optimal circulation time of the complexes is achieved with a reach and deliver greater than 90% of the complexes to the target cells in the first pass, avoid uptake in non-target tissues, and efficiently interact with the cell surface to produce optimal transfection.

FIG. 26*a* shows optimal transfection of the lung and heart after intravenous (IV) injection of BIVs encapsulating a plasmid encoding CAT with no masking agent in SCID mice. FIG. 3 shows the optimized strategy that was used to achieve targeted delivery, including deshielding by reversible masking, fusion with the cell membrane, and entry of the therapeutic or imaging agent into the cell and to the nucleus (if desired).

Screening of the Exploratory Library: This library of 150 dimers has been tested using high-throughput in vitro screening in MCF-7 human breast cancer cells, A549 human lung cancer cells, PANC1 and Mia PaCa2 human pancreatic cancer cells, in human tumor endothelium of H1299 human small cell lung cancer cells, in human tumor endothelium of PANC1 human pancreatic cancer cells, and in the corresponding normal cell types. BIVs were prepared using our unique manual extrusion of DOTAP:synthetic cholesterol (50:45) [1] [1]. We prepared functionalized complexes by mixing BIV complexes with the bivalent compounds (ligand-coated BIV complexes) bearing hydrocarbon tails and incubating O/N. Upon incubation, the hydrocarbon tails spontaneously insert into the surface lipid bilayers of BIV complexes. Each of these bivalent compounds were added at surface concentrations ranging from 1×10-1-$10^4$ pg per ug of therapeutics (e.g. chemotherapeutic drugs, gene therapeutics) or reporters (luciferase encoding plasmid). For in vivo studies, complexes are filtered through a 1.0 uM polysulfone filter (Whatman) prior to adding the small molecule ligands and masking agents are added to ligand coated-BIV complexes prior to intravenous injections as described above. Control studies were used to identify monovalent or bivalent ligands that direct the BIVs to cancerous cells selectively over normal cells or to tumor endothelium versus normal endothelium.

All cell types have hundreds or even thousands of cell surface receptors (most of which are unidentified to date), and the proposed approach interrogates all of them to identify the optimal ligand-receptor interaction in each well. Bivalent compounds that "pass" this screen are incorporated into reversibly masked BIV-complexes that encapsulate imaging agents or therapeutics to image and/or destroy tumors and their metastases or to tumor endothelium in vivo. The approach is therefore extremely direct with respect to delivery of therapeutic materials or imaging agents to different cancer cells in vivo.

Cell surface receptors can be identified that bind to the ligands that provide the most successful targeted delivery. These ligands can be immobilized on affinity columns, and solublized cell extracts can be passed over the columns. The bound material can assessed for protein identification by mass spectrometry and database analyses. If the receptor that we identify is a known signaling receptor, then we can also investigate whether our ligand activates or inhibits activation of that receptor.

Positive Hits: Significant positive hits (hits) were obtained using compounds #1035, 1036, 1039, 1063, 1064, 1066, and 1067 coated on the surface of BIV complexes in transfections of MCF-7 cells. Whereas, in A549 cells, hits were found using compounds #1001, 1003, 1042, 1051, 1062, 1096, 1107, 1108, and 1029. FIG. 9 is a graph that shows the transfection efficiency of the listed compounds against A549 cells. Hits were defined as those compounds that increased transfection by at least 100% (+2 on the Y axis) over transfections using BIV complexes alone. The greatest hit observed produced nearly a 300% (+4 on the Y axis) increase in transfection efficiency. These hits were not found in screening MCF-10A cells, the normal or near-normal counterpart cell line to MCF-7. FIG. 8 is a graph that shows the transfection efficiency of the listed compounds against MCF7 cells. MCF-10A cells are often used as the near normal control cell line because they are human mammary gland cells that have a normal or near-normal karyotype (Reference: Soule, H D, et al. (1990). Isolation and characterization of a spontaneously immortalized human breast epithelial cell line, MCF-10. *Cancer Res* 50: 6075-6086. FIG. 10 is a graph showing the transfection efficiency of the listed compounds against MCF10A cells. For the pancreatic cell screening, the results below showed statistically significant hits for PANC1 and Mia PaCa2 cells that were not found on the normal cells, HPDE. FIGS. 11, 12, and 13 show the relative luciferase expression in PANC1, Mia PaCa2, and HDPE cells, respectively. Only one compound, KB-995, showed hits on both cell lines. Co-culture of HUVEC+ human tumor cells showed transitions to tumor endothelium after 8 days in co-culture both for H1299 lung cancer cells and PANC1 pancreatic cells. This was demonstrated by increased CD31+ on the endothelial cell compartment by flow cytometry, and upregulated VEGFA in the co-cultures and not in HUVEC (data not shown here). Data from the in vitro screens showed hits using KB1116, KB1063, or KB1123 for transfection of H1299 tumor endothelium and not for HUVEC or for H1299. FIGS. 14 and 16 show the transfection enhancement in a co-culture of HUVEC and HI299 cells and HUVEC cells alone with the compounds presented herein. FIG. 15 shows the transfection results in a culture of HI299 cells alone with the compounds of the present invention, no enhancement was noted. Whereas, hits for PANC1 tumor endothelium were produced using different compounds, KB1124 or KB1125. These compounds also did not produce hits when screening HUVEC or PANC1.

EXAMPLE 1

Anti-angiogenesis can be an effective cancer therapy if directed to the tumor vasculature. We achieved targeted delivery of a non-viral gene therapeutic to human tumor vasculature by attachment of tumor endothelium-specific ligands to the surface of our unique bilamellar invaginated liposomal complexes used in conjunction with reversible masking to bypass non-specific tissues and organs. Small molecules were identified that enhanced transfection efficiency of tumor endothelial cells, but not normal endothelial cells or cancer cells. Intravenous administration of our targeted, reversibly masked complexes to human tumor endothelium-pancreatic tumor bearing mice specifically increased transfection to the tumor endothelium. Efficacy studies using our optimized targeted delivery of a plasmid encoding thrombospondin-1 significantly inhibited tumor growth. Therefore, these small molecules specifically target pancreatic or lung tumor endothelium, and therefore have the potential to be used successfully in anti-angiogenic cancer therapy.

Angiogenesis, the process of new blood vessel formation, is required for sustained cancer growth and metastasis [26, 27]. Recent approval of antiangiogenic drugs (e.g. Bevacizumab, Sorafenib and Sunitinib) by the FDA supports the use of anti-angiogenesis as a strategy for the treatment of cancer [28,29]. Delivery vehicles used for gene therapy include viral, non-viral, and bacterial vectors (Reviewed in: [30]). Other delivery methods such as in vivo electroporation, ballistic and other needle-free delivery systems are also used (Reviewed in: [30]). Much work has focused on the use of non-viral vectors due to diminished safety concerns and ease of manufacturing. Non-viral vectors have been used successfully in many pre-clinical and clinical studies (Reviewed in: [30]), [31-34].

It is demonstrated herein that targeted delivery using small molecules in conjunction with our reversible masking technology was be used to bypass uptake in non-target organs (Templeton, N. S. U.S. Pat. No. 7,037,520 B2 issued May 2, 2006). A combinatorial library developed in lab of Burgess allows production of small molecules designed to bind proteins selectively [35-38]. Members of the library resemble secondary structure motifs found at hot-spots in protein-ligand interactions, e.g. bivalent beta-turn mimics designed to have an affinity for cell surface receptors. Importantly, the bivalent small molecules can have selectivity for binding cell surface receptors. Here the strategy was adapted to produce bivalent molecules that have hydrocarbon tails, and preparation of functionalized BIV complexes from these is fast and routine in our lab.

Finally, the efficacy studies focused on the targeted delivery of plasmid DNA encoding the anti-angiogenic protein, human thrombospondin-1 (TSP1). TSP1 is a secreted protein that can prevent angiogenesis, the formation of new blood vessels required to sustain tumor growth [39]. The modified TSP1 mimetic ABT-510 has advanced to Phase II clinical trials to treat advanced cancer [39]. Recent studies have also shown that gene delivery of TSP1 significantly inhibits growth of various cancers and tumor microvessel density in animal models [32, 33, 40-42]. It is demonstrated herein that targeted, reversibly masked delivery of a TSP1 expression plasmid significantly improves the efficacy of TSP1 gene therapy.

Preparation of BIV DNA:Liposome Complexes: Plasmid pCMV-THBS-1 encodes the TSP1 gene. Plasmid DNA was purified by anion exchange chromatography. DOTAP and DOTAP:Chol BIV liposomes, BIV DNA:liposome complexes (BIV complexes) were prepared as previously described [43], except that synthetic cholesterol was used at a ratio of 50:45 DOTAP:cholesterol.

Bivalent Small Molecule Production: Briefly, through selective coupling the β-turn monovalent small molecules were mixed in solution to produce homodimer, KB991-KB1005, and heterodimer, KB1006-KB1140, bivalent small molecules. During the process, only potassium carbonate was required to affect the coupling. Boc-protected monomeric compounds were treated with 30% TFA in $CH_2Cl_2$ for 4 h at 25° C. The solvent was removed and residue was re-dissolved in DMSO to make a solution of 0.03 M. The dichlorotriazine linker scaffold and $K_2CO_3$ were sequentially added. The resulting suspension was sonicated for 15 min and rocked for 7 days. DMSO was lyophilized, and aqueous HCl solution (5%, about 0.5 mL) was added to the above solid residue and sonicated for 3 min. Most of the compounds were precipitated in acidic solutions. After centrifugation, the pellets were dried and saved. In order to coat the monovalent or bivalent small molecules onto the surface of BIV complexes, a hydrocarbon tail was included in the molecules for insertion into the surface lipid bilayer. Compounds (about 10.0 mg) were initially dissolved in 1.0 mL THF/$H_2O$ (v:v=1:1). $CuSO_4$ solution (1.0 M, 10 μL) was added and followed by Cu powder (1.0 mg). After that procedure, azidooctadecane in THF solution (0.1 mmol, 0.2 mL) was added, and the resulting suspension was stirred at 25° C. for 24 h. The suspension was filtered through a glass pipette filled with silica gel using 30% methanol in $CH_2Cl_2$ as eluents. The solution was dried and concentrated to the final products. After synthesis, the solid compounds were dissolved in 1:1 chloroform:methanol in glass test tubes. Thin films were produced at the bottom of the tubes under a steady stream of argon gas under the tissue culture hood. The films were dissolved in sterile water to produce a 5 mg/mL stock and subjected to sonication (Lab-Line Trans-sonic 820/H) at 50° C. Aliquots of the reconstituted compounds were stored at −80° C.

Figure 24:
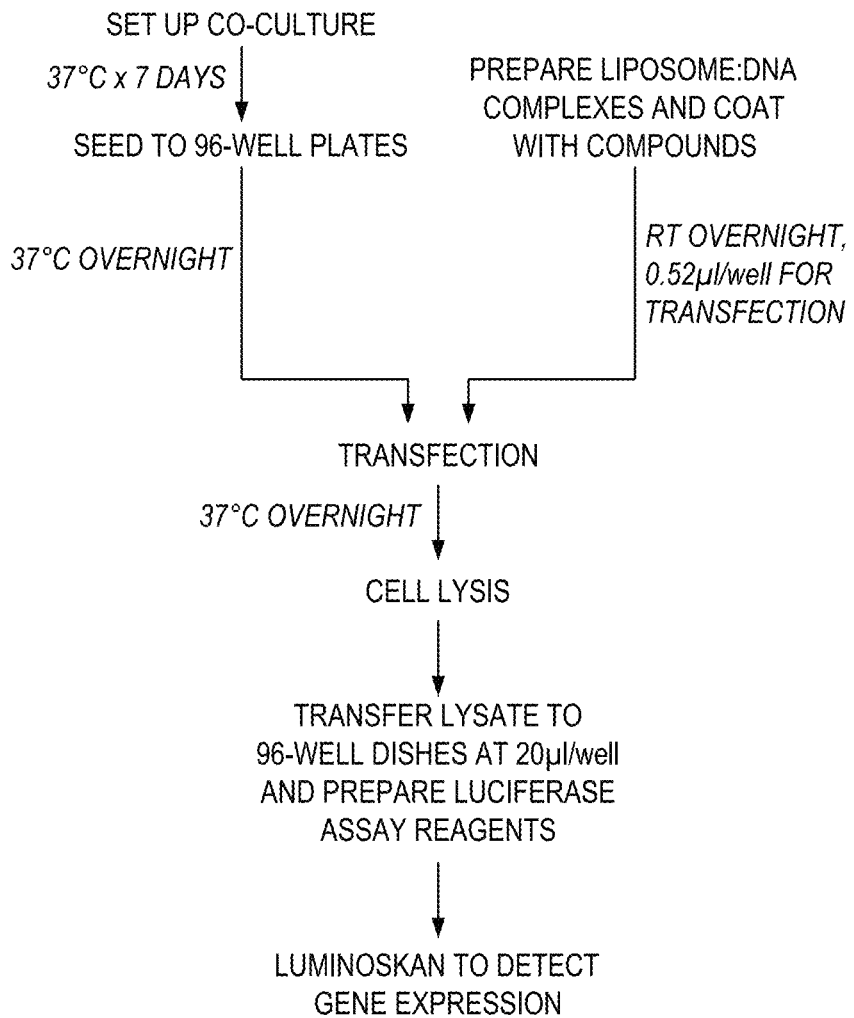
FIG. 24 is a flowchart of a method of the present invention.

FIG. 24. In Vitro Delivery and High Throughput Luciferase Assay: A high throughput assay was used to identify monovalent or bivalent compounds attached to the surface of BIV complexes that internalize into tumor vascular endothelial cells more efficiently than non-targeted BIV complexes.

In Vivo Targeted Delivery and CAT Assay: At 8 weeks post-IP injections of co-cultures detailed above, BIV-CAT DNA complexes were prepared and coated with the small molecule KB1023 at 500 pg compound/μg DNA as discussed above. The complexes were mixed with various concentrations of reversible masking reagent, n-dodecyl-beta-D-maltopyranoside (Anatrace, Maumee, Ohio), just prior to intravenous (IV) injections into mice. Each mouse was injected with a total volume of 110 µL complexes containing 50 µg of p4119 CAT DNA. At 14 h post-IV injection, mice were sacrificed, tissues were harvested, and total protein was extracted as previously described [43]. CAT protein production was measured using the CAT ELISA kit (Roche, Indianapolis, Ind.) following the manufacturer's instructions. Protein concentration was determined using the Micro BCA kit (Pierce) following the manufacturer's instructions.

Anti-Angiogenic Cancer Therapy: At 2 weeks post-IP injections of the co-cultures detailed above, in vivo delivery was performed using the protocol described above, except that 35 µg TSP1 plasmid DNA was encapsulated in the BIV-KB1023 coated complexes and 11 mM reversible masking reagent was used prior to IV injections. Injections were performed once every two weeks for a total of three injections. In a different group, injections were performed weekly for a total of five injections. Two weeks after the final injection (8 weeks post-IP injection of the co-cultures to establish the tumor model), the mice were sacrificed and tumor size was measured. Intra-abdominal tumors and other organs (liver, lungs, spleen, pancreas and colon) were dissected followed by fixation in 10% neutral buffered formalin.

In vitro human tumor endothelium model: Tumor cells secrete growth factors and cytokines to initiate and stimulate angiogenesis for their growth (Reviewed in [44]). Therefore, an in vitro human tumor endothelium model was established by co-culturing human umbilical vein endothelial cells (HUVEC) with human H1299 non-small cell lung carcinoma cells (H1299 co-cultures) or human PANC1 ductal pancreatic adenocarcinoma (PANC1 co-cultures).

Small molecule libraries for targeted delivery: A prepared library of 15 homodimer and 135 heterodimer bivalent compounds that are "semi-peptidic" β-turn analogs was used. Significantly, these compounds can incorporate any amino acid side chains, so they can be designed to mimic turns at any hot spot that involves that motif. These compounds are different than other compound libraries that have been prepared before insofar as they have polar "warhead" functionalities (mimics 1 and 2) [45] and hydrophobic tails. The small molecule peptidomimetics used in prior studies are active against some protein-protein interaction targets which have β-turn hot-spots [36, 37]. One of the compounds bound to TrkA receptors on neurons and has applications for stroke recovery and neurodegenerative disorders including dementia [38, 46]. For the custom libraries used in our work, two monovalent mimics were combined through chemical steps requiring only potassium carbonate for coupling to form bivalent homodimers and heterodimers. This modification greatly enhances the affinity of the compounds for cell surface receptors. Unlike most combinatorial syntheses, no protecting groups are involved in the last steps of this approach, so the final product does not have to be purified from protecting group residues and added scavenger materials. A hydrocarbon tail was structurally incorporated for coating of the compounds to the surface of liposomal complexes.

High-throughput in vitro screening: A novel, high-throughput luciferase assay was developed to screen the small molecule libraries for tumor endothelium targeting ligands. Highly sensitive and accurate detection systems are required for successful high throughput screens. Furthermore, delivery into the cell nucleus for the detection of potential ligand binding and internalization across the cell membrane is most direct and ultimately reliable. Luciferase expression produced by plasmid DNA delivered to the nucleus meets these criteria.

Figure 17:
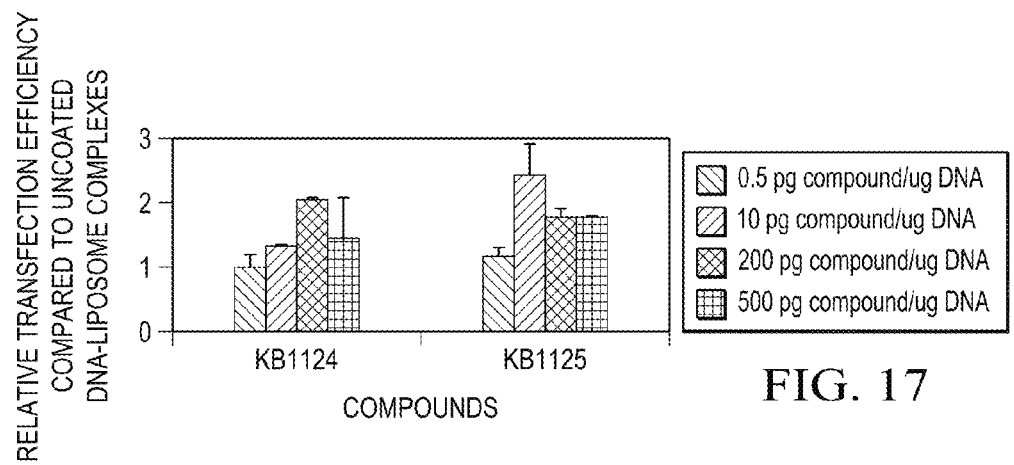
FIG. 17 shows the shows the transfection enhancement in a co-culture of HUVEC and PANC1 cells with the listed compounds.
Figure 18:
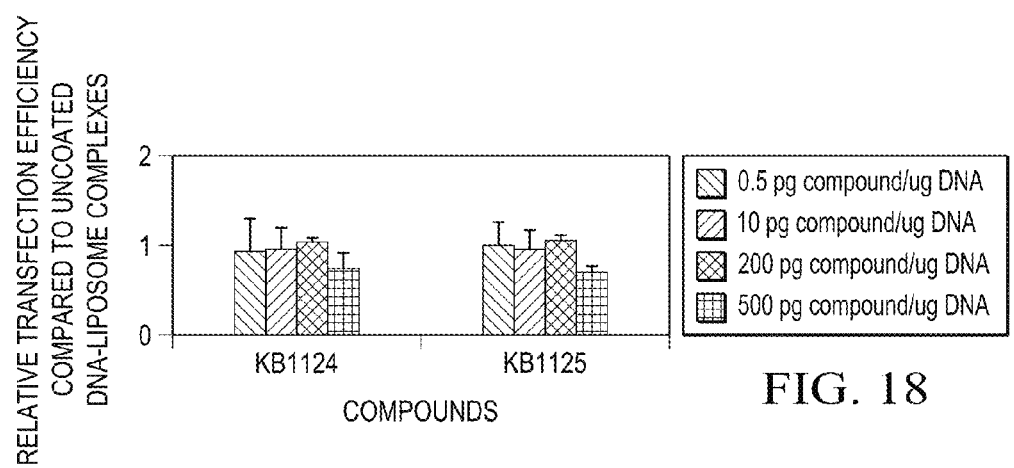
FIG. 18 shows the shows the transfection results in a culture of PANC1 cells alone with the listed compounds, no enhancement was noted.
Figure 19:
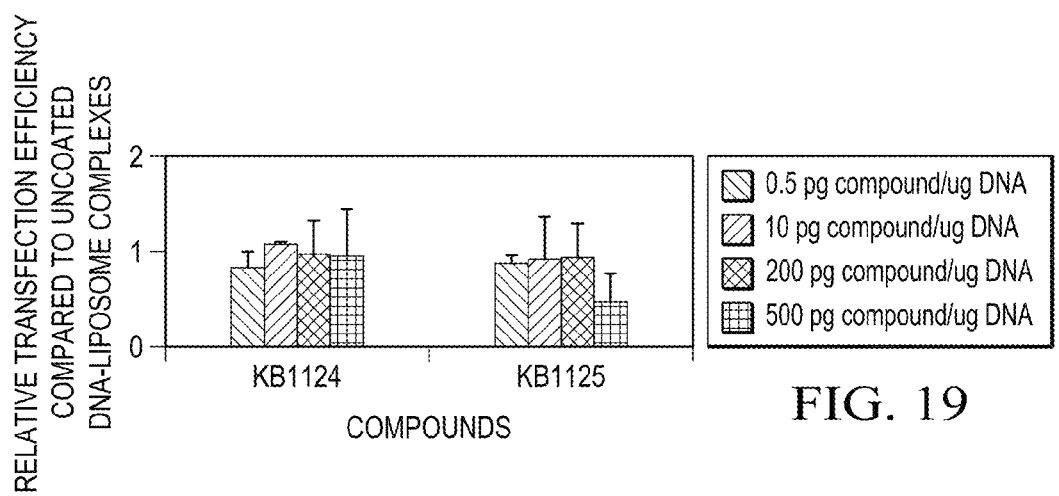
FIG. 19 shows the shows the transfection results in a culture of HUVEC cells alone with the listed compounds, no enhancement was noted.
Figure 23A:
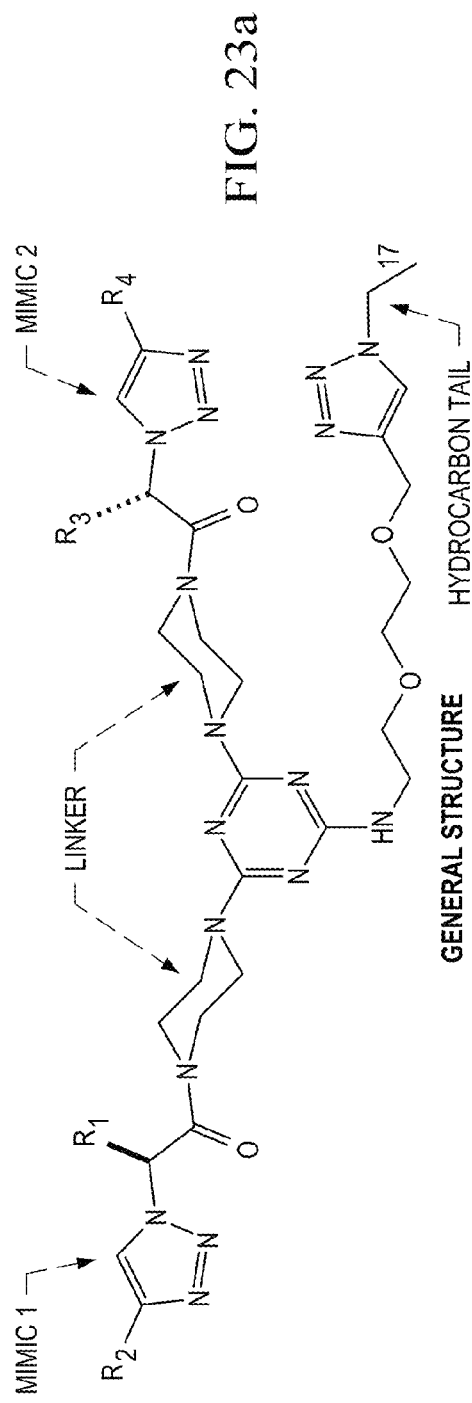
FIGS. 23a and 23b. Bivalent small molecule structure and library screening. The general structure of the bivalent small molecule (23a) includes two β-turn mimics for interaction with cell surface receptors, a hydrocarbon tail for insertion into BIV liposomal complexes, and a linker. The structure of our "hit" molecule, KB1023, is also shown. A high-throughput luciferase assay (23b) was used to screen for tumor endothelial cell-specific targeting ligands. At 7 days after co-culture, cells were harvested and seeded to 96-well plates at $2 \times 10^4$ cells/well. On the same day, BIV-luciferase DNA:liposome complexes were prepared followed by coating of compounds at various compound:DNA ratios. The coated complexes were incubated at RT overnight. The following day, cells were transfected with 50 μL of serum free medium that contained 0.52 μL coated complexes. Transfection was ended by replacing the transfection medium with cell culture medium containing serum. At 24 h post-transfection, cells were lysed and the cell lysate was loaded to 96-well plates at 20 uL/well for luciferase assay using the Luminoskan plate reader.
Figure 23B:
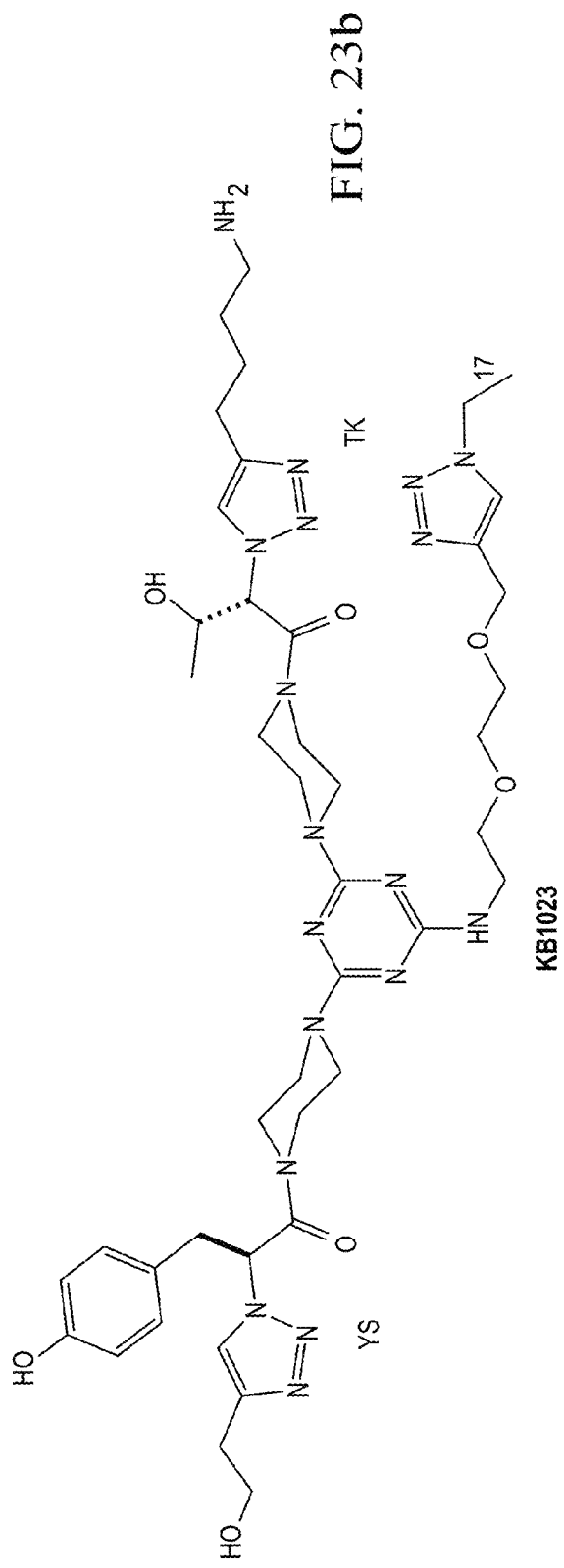

The co-cultures versus cancer cells versus HUVECs were screened in vitro against the bivalent and monovalent small molecule libraries using our high-throughput screen. Hits were defined as those compounds that increased transfection of the luciferase plasmid by at least 100% (+2 on the Y axis) over transfections using BIV complexes alone. In screening the libraries, we identified a compound KB1023 that specifically enhanced the transfection efficiency by 100% in the PANC1 co-culture (FIG. 17), but not in PANC1 cells (FIG. 18) or HUVEC (FIG. 19) alone. The structure of KB1023 is shown in FIG. 23b.

To further verify that increased transfection was observed only for the vascular endothelial cells of the co-culture, growth of PANC-1 cells and HUVECs was performed for 8 days in transwell plates with HUVECs grown in the bottom well. Data shown in FIG. 17 verified that indeed increased transfection was produced only for the vascular endothelial cells of the co-culture by the KB1023 coated BIV-luciferase DNA complexes. Other human pancreatic cell lines were co-cultured with HUVECs and transfected using KB1023 for increased delivery. Only AsPC1 cells showed significant increased transfection, whereas miaPaCa2 and BxPC3 cells did not (data not shown). These data suggest that expression of targeting molecules on tumor endothelium may differ among pancreatic carcinomas.

EXAMPLE 2

Targeted Delivery of Liposomal Complexes for Anti-Angiogenic Cancer Therapy. Anti-angiogenesis can be an effective cancer therapy if directed to the tumor vasculature. We achieved targeted delivery of a non-viral gene therapeutic to human tumor vasculature by attachment of tumor endothelium-specific ligands to the surface of our unique bilamellar invaginated liposomal complexes used in conjunction with reversible masking to bypass non-specific tissues and organs. An in vitro human tumor vasculature model was created by co-culturing primary human endothelial cells with human lung or pancreatic cancer cells. The model was confirmed by increased expression of tumor endothelial phenotypes including CD31 and VEGF-A, and prolonged survival of endothelial capillary-like structures. The co-cultures were used for high-throughput screening of a specialized small-molecule library to identify tumor endothelium-specific ligands. We identified small molecules that enhanced transfection efficiency of tumor endothelial cells, but not normal endothelial cells or cancer cells. Intravenous administration of the targeted, reversibly masked complexes of the present invention to human tumor endothelium-pancreatic tumor bearing mice specifically increased transfection to the tumor endothelium. Efficacy studies using our optimized targeted delivery of a plasmid encoding thrombospondin-1 significantly inhibited tumor growth. It was found that these small molecules specifically target pancreatic or lung tumor endothelium and are useful in anti-angiogenic cancer therapy.

Figure 20A:
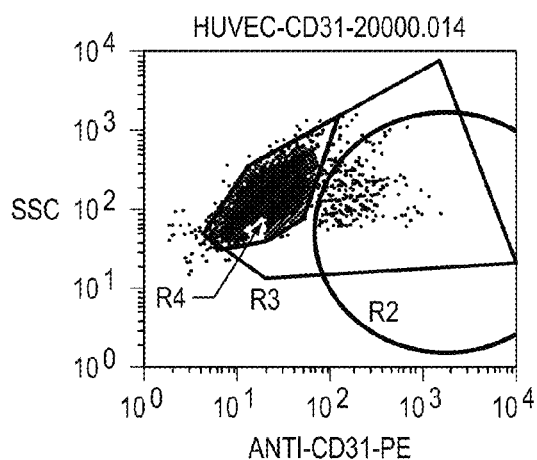
FIGS. 20a to 20c. Increase in endothelial CD31+ expression after co-culture. We established co-cultures at a plating ratio of 30:1 HUVEC:H1299 after counting the cells. Endothelial cells were stained by phycoerythin-conjugated anti-CD31 Ab and the endothelial cell population (gated by R3) was measured using flow cytometry post-seeding on a daily basis. The vast majority of the endothelial cells expressed low levels of CD31 (gated by R4). A few endothelial cells expressed a high level of CD31 (gated by R2). At 8 days after co-culture, the endothelial cell population of the co-culture significantly increased in CD31 expression compared to that of the HUVEC control (c). The enhancement in CD31 expression was far greater after 9 days in co-culture (b, c) compared to the HUVEC control (a, c). *P=0.026.
Figure 20B:
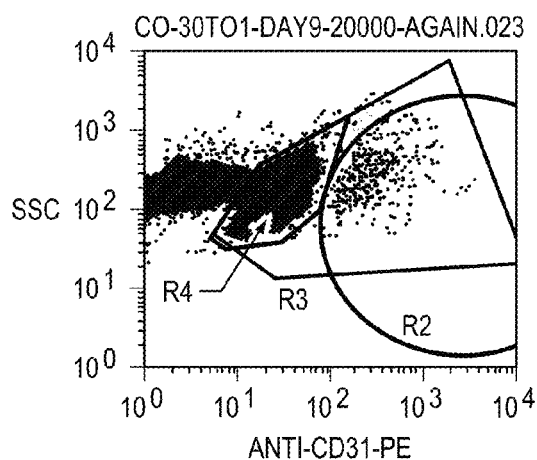
Figure 20C:
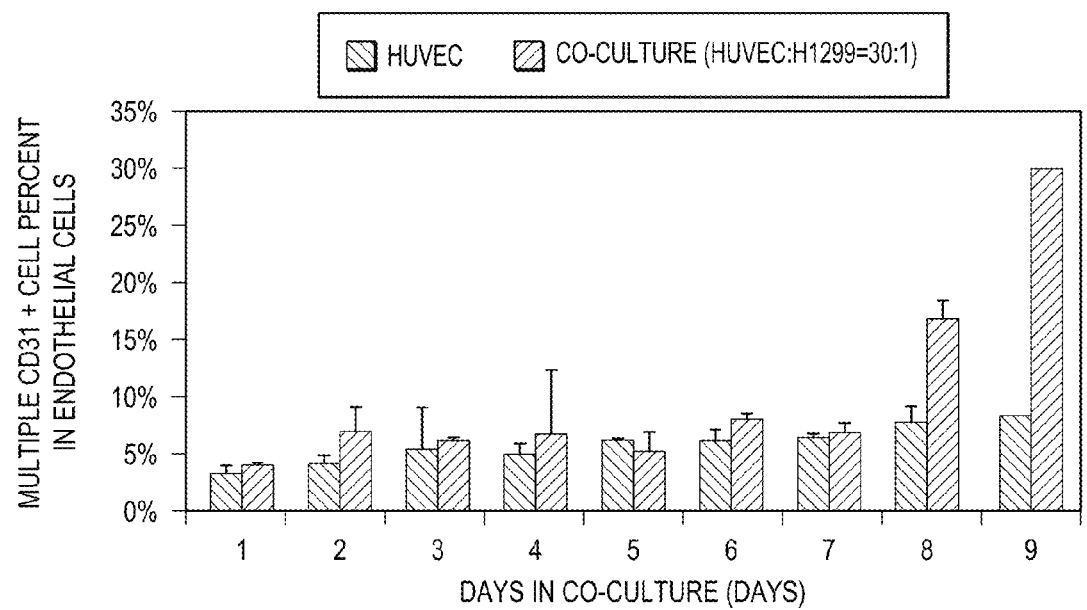

Human tumor endothelium in vitro and in vivo mouse model. Tumor cells secrete growth factors and cytokines to initiate and stimulate angiogenesis for their growth. Therefore, an in vitro human tumor endothelium model was established by co-culturing human umbilical vein endothelial cells (HUVEC) with human H1299 non-small cell lung carcinoma cells (H1299 co-cultures) or human PANC1 ductal pancreatic adenocarcinoma (PANC1 co-cultures). We first looked for changes in the endothelial markers over time to indicate the transition of normal endothelium to tumor vasculature endothelium. Published literature suggested that an increase in CD31 on the endothelial cells can occur at this transition as detected by flow cytometry [30]. The flow cytometry data (FIGS. 20b,c) shows that this transition occurs between days 8 and 9 in co-culture with H1299 cells. A majority of the HUVECs expressed low levels of CD31 (FIG. 20a, gated by R4). Only few HUVECs expressed high levels of CD31 (gated by R2). After 8 days in the H1299 co-culture, the percentage of high level, CD31 expressing endothelial cells increased by 113% compared to that of the HUVEC control (FIG. 20b; 16.86% versus 7.9%). The increased CD31 expression was significantly higher at 264% after 9 days in co-culture compared to the HUVEC controls (FIG. 20c; 29.96% versus 8.23%).

Figure 21A:
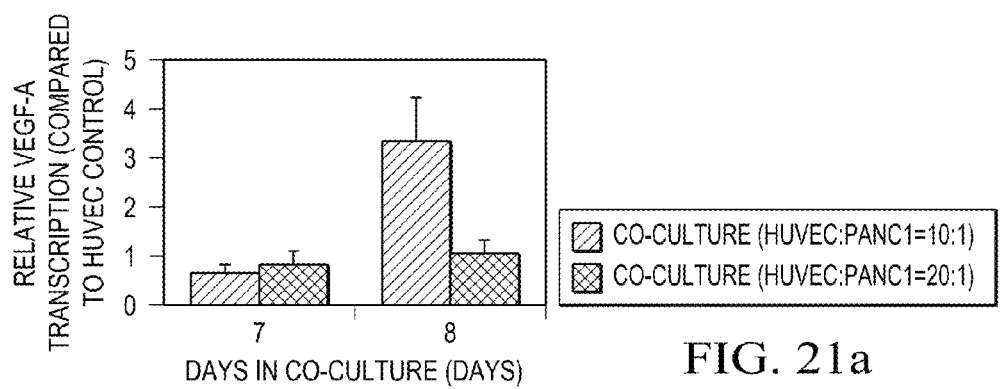
FIGS. 21a and 21b. Enhanced endothelial VEGF-A expression after co-culture. Co-cultures were established at a plating ratio of 10:1 HUVEC:PANC1 and cultivated in two-chamber transwell dishes for 8 days. Endothelial cells were harvested and VEGF-A expression was measured using real-time RT-PCR and Western blotting. Endothelial VEGF-A expression increased at transcriptional (a) and translational (b) levels after co-culture compared to that of the HUVEC control. *P<0.01, N=6.
Figure 21B:
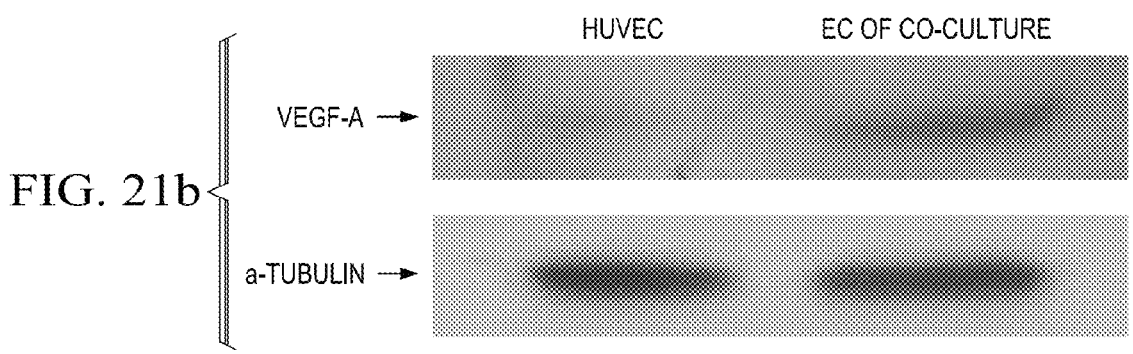

A VEGF-A autocrine loop is activated in tumor vasculature, and expression of the VEGF receptors and VEGF-A are increased at both the mRNA and protein levels [31]. VEGF-A is also a key pro-angiogenic factor and stimulates endothelial cell proliferation and migration, prolongs endothelial cell survival, and sustains capillary-like tubular structures that are formed by endothelial cells [32, 33]. FIG. 21 shows increased expression of VEGF-A as detected by quantitative RT-PCR (FIG. 21a; 225%) and by Western blotting (FIG. 21b; 160%) in PANC-1 co-cultures at day 8 in co-culture in two-chamber transwell plates with 0.4 µm-sized microporous membranes.

Figure 22A:
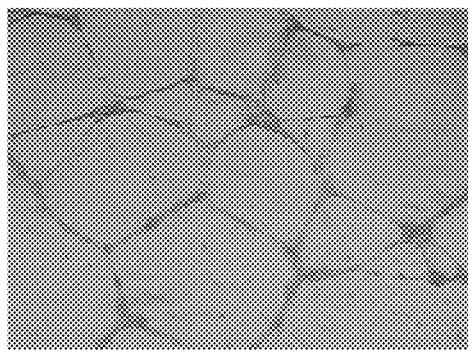
FIGS. 22a to 22f. Prolonged tube survival after co-culture. At 8 days after co-culture in transwell dishes at a plating ratio of 10:1 HUVEC:PANC1, endothelial cells were harvested and seeded on Matrigel. At 16 h later, both the HUVEC control (a) and endothelial cells of the co-culture (b) form capillary-like tubular structures. These structures started to degrade 48 h later. By 72 h, the tubular structure of the HUVEC control was almost completely degraded (c). However, in the co-culture a significant amount of tubular structures survived (d). These structures maintained an excellent tubular network and survived for 11 more days (e, f).
Figure 22B:
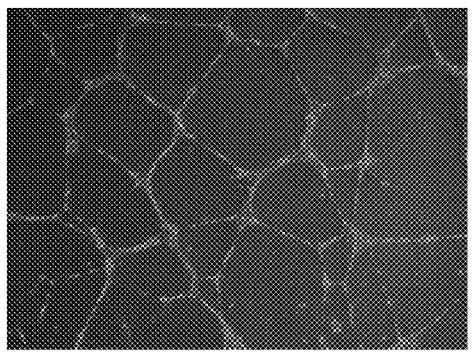
Figure 22C:
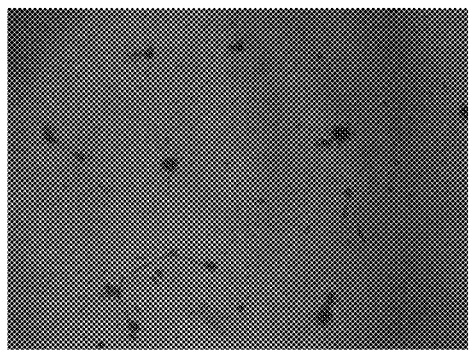
Figure 22D:
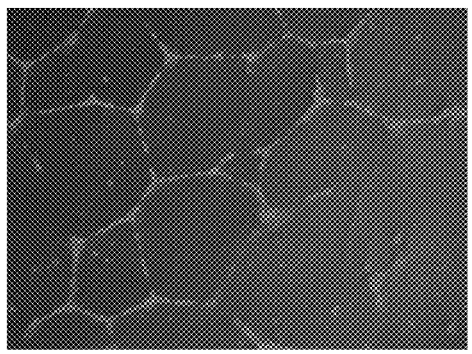
Figure 22E:
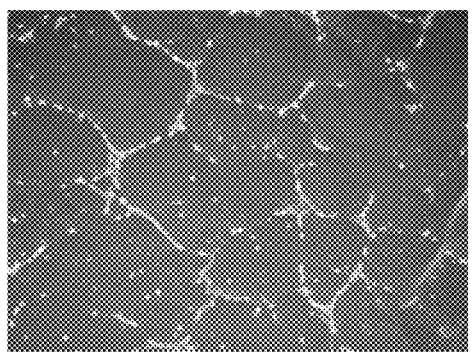
Figure 22F:
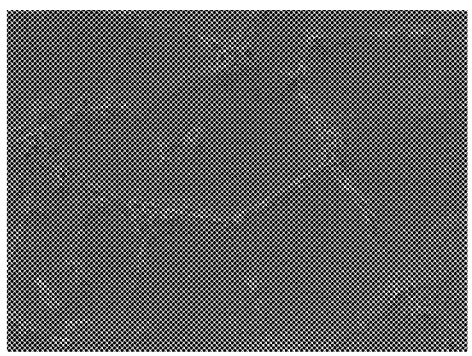

When plated on Matrigel, endothelial cells transiently form capillary-like tubular networks in vitro. At 16 hours (h) after plating on Matrigel, our assays showed no significant difference in tube formation between HUVECs (FIG. 22a) and endothelial cells of the PANC1 co-cultures (FIG. 22b; co-cultured for 8 days in transwell plates). The tubular structure of the HUVEC control started to degrade at 48 h and by 72 h was almost completely degraded (FIG. 22c). In contrast, a significant amount of tubular structure survived at 72 h in endothelial cells from the PANC1 co-culture (FIG. 22d) and continued to survive for 11 more days (FIG. 22e-f). When the PANC1 cell inserts were removed from the transwell plates, no difference in tube survival between the endothelial cells separated from the PANC1 co-culture and the HUVECs was detected. These data demonstrate that factors produced by co-culture with the cancer cells prolong the survival of the endothelial tubular structure of the co-culture, perhaps due to increased VEGF-A expression.

Figure 4:
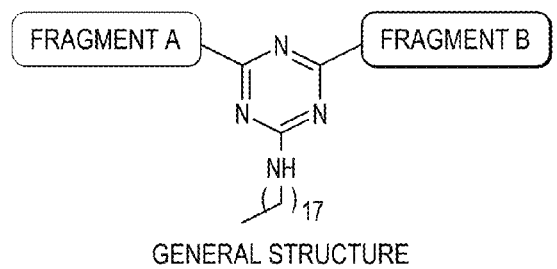
FIG. 4 shows the structures of the various compounds of the present invention, the general structure is shown on top, with the specific structures listed from left to right, KB991-KB1005, respectively.
Figure 4:
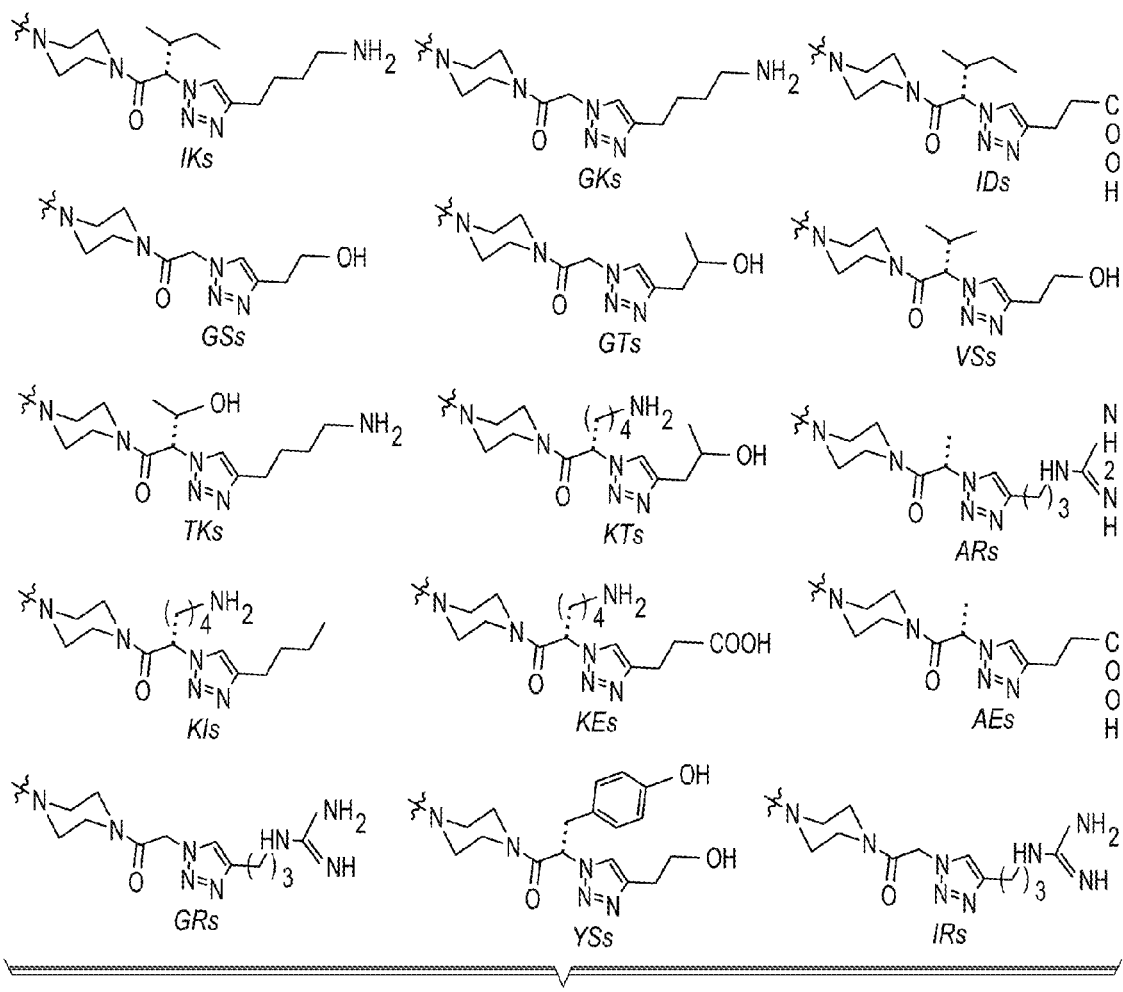
Figure 6:
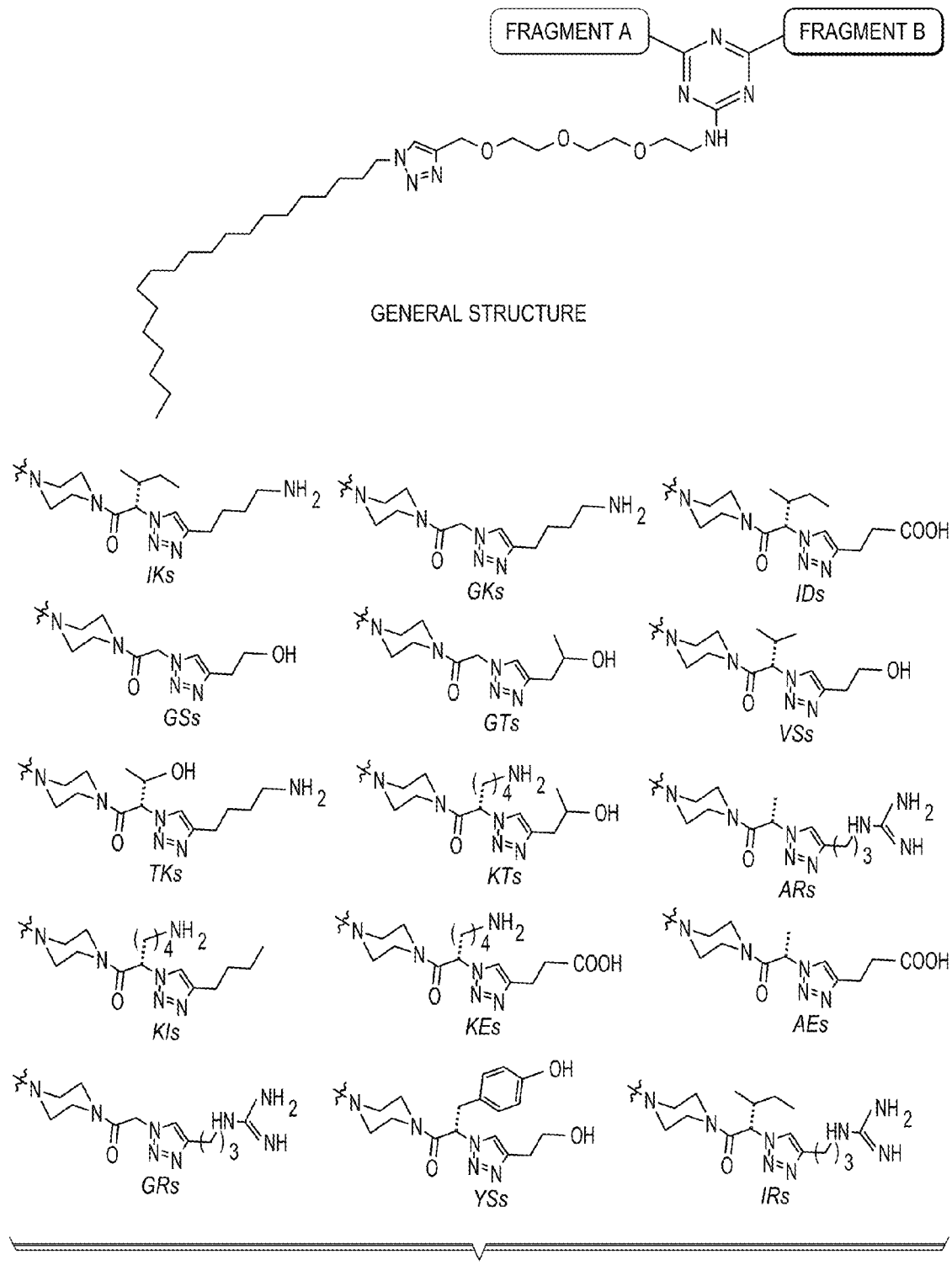
FIG. 6 shows one example of a structure of the present invention, the general structure is shown on top, with the specific structures listed from left to right, KB991-KB1005, respectively.
Figure 7A:
Figure 10:
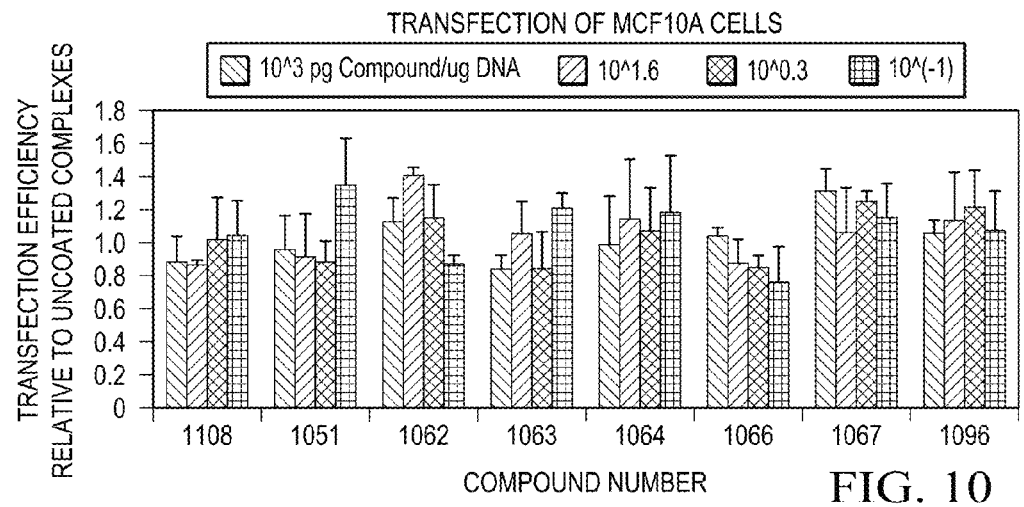
FIG. 10 is a graph that shows the transfection efficiency of the listed compounds against MCF10A cells.

High-throughput in vitro screening of small molecule libraries for targeted delivery. The libraries of 15 homodimer and 135 heterodimer bivalent compounds that are "semi-peptidic" β-turn analogs were screened. Their general structure is shown in FIG. 4. In FIG. 4, the general formula is shown on top, with the specific structures named KB991-KB1005 shown from left to right, respectively. Significantly, these compounds can incorporate any amino acid side chains, so they can be designed to mimic turns at any hot spot that involves that motif. These compounds are different than other compound libraries that have been prepared before insofar as they have polar "warhead" functionalities (mimics 1 and 2) and hydrophobic tails. The small molecule peptidomimetics used in prior studies are active against some protein-protein interaction targets which have β-turn hot-spots. One of the compounds bound to TrkA receptors on neurons and has applications for stroke recovery and neurodegenerative disorders including dementia. For the custom libraries used in our work, two monovalent mimics were combined through chemical steps requiring only potassium carbonate for coupling to form bivalent homodimers and heterodimers). It was found that this modification greatly enhances the affinity of the compounds for cell surface receptors. Unlike most combinatorial syntheses, no protecting groups are involved in the last steps of this approach, so the final product does not have to be purified from protecting group residues and added scavenger materials. A hydrocarbon tail was structurally incorporated for coating of the compounds to the surface of liposomal complexes.

A novel, high-throughput assay was developed to screen the small molecule libraries for tumor endothelium targeting ligands (FIG. 24). Highly sensitive and accurate detection systems are required for successful high throughput screens. Furthermore, delivery into the cell nucleus for the detection of potential ligand binding and internalization across the cell membrane is most direct and ultimately reliable. Luciferase expression produced by plasmid DNA delivered to the nucleus meets these criteria; it is a straight-forward, and well-established technology. A Luminoskan Ascent plate luminometer was used (Thermo Labsystems) to achieve highly sensitive high-throughput quantitation of transfection efficiency.

Figure 25A:
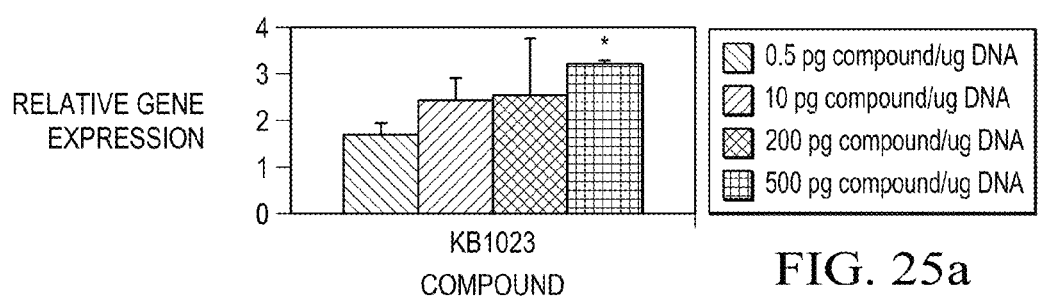
FIGS. 25a to 25h. Pancreatic and lung tumor endothelium targeting ligands. Compound KB1023 increased the transfection efficiency of the PANC1+HUVEC co-culture (a), but not PANC1 cells (b) or HUVECs (c). Targeting was confirmed for the endothelium compartment of the co-culture (d) using a two-chamber transwell culture system. KB1023 also increased the transfection efficiency of endothelial cells after coculture with AsPC1 cells (e). KB1061 enhanced the transfection efficiency in the co-culture of H1299 and HUVEC (f), but not in H1299 cells (g) or HUVECs (h). Luciferase gene expression was compared to that of uncoated liposomal complexes. *P<0.05.
Figure 25B:
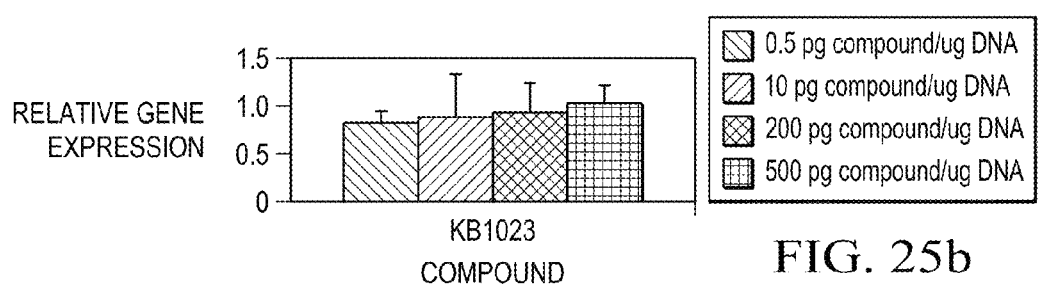
Figure 25C:
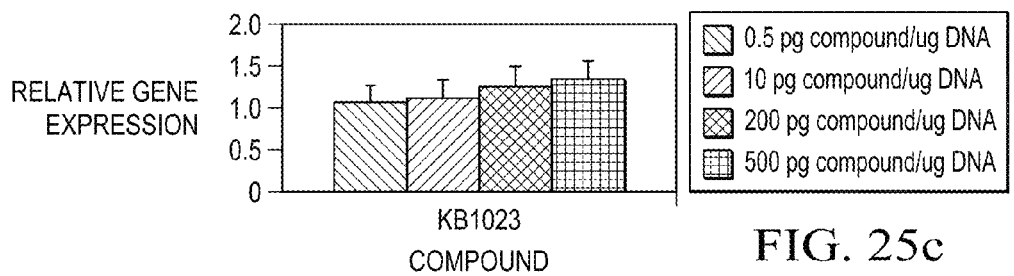

The co-cultures versus cancer cells versus HUVECs were screened in vitro against the bivalent and monovalent small molecule libraries using our high-throughput screen. Hits were defined as those compounds that increased transfection of the luciferase plasmid by at least 100% (+2 on the Y axis) over transfections using BIV complexes alone. In screening the libraries, we identified a compound KB1023 that specifically enhanced the transfection efficiency by 100% in the PANC1 co-culture (FIG. 25a), but not in PANC1 cells (FIG. 25b) or HUVEC (FIG. 25c) alone. The general structure of the bivalent small molecule is shown in FIG. 23a that includes two β-turn mimics for interaction with cell surface receptors, a hydrocarbon tail for insertion into BIV liposomal complexes, and a linker. The structure of KB1023 is shown in FIG. 23b.

Figure 25D:
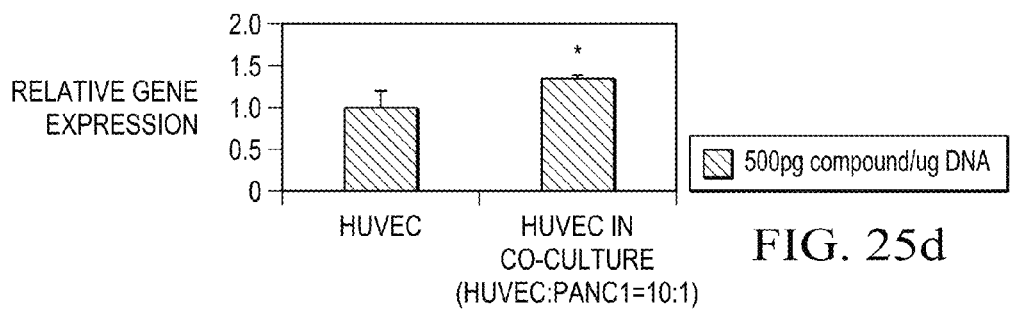
Figure 25E:
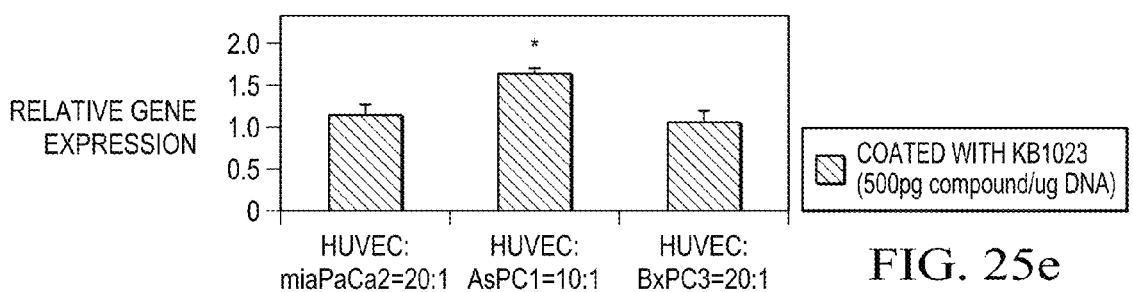

To further verify that increased transfection was observed only for the vascular endothelial cells of the co-culture, growth of PANC-1 cells and HUVECs was performed for 8 days in transwell plates with HUVECs grown in the bottom well. Data shown in FIG. 25d verified that indeed increased transfection was produced only for the vascular endothelial cells of the co-culture by the KB1023 coated BIV-luciferase DNA complexes. Other human pancreatic cell lines were co-cultured with HUVECs and transfected using KB1023 for increased delivery. Only AsPC1 cells showed significant increased transfection, whereas miaPaCa2 and BxPC3 cells did not (FIG. 25e). These data suggest that expression of targeting molecules on tumor endothelium may differ among pancreatic carcinomas.

Figure 25F:
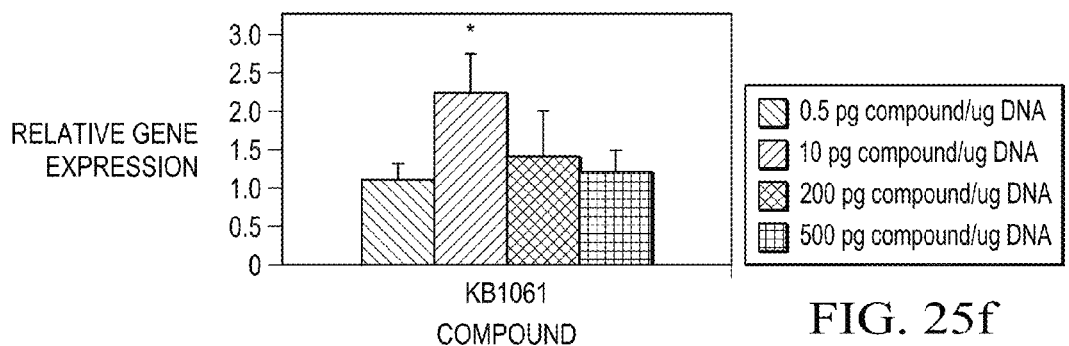
Figure 25G:
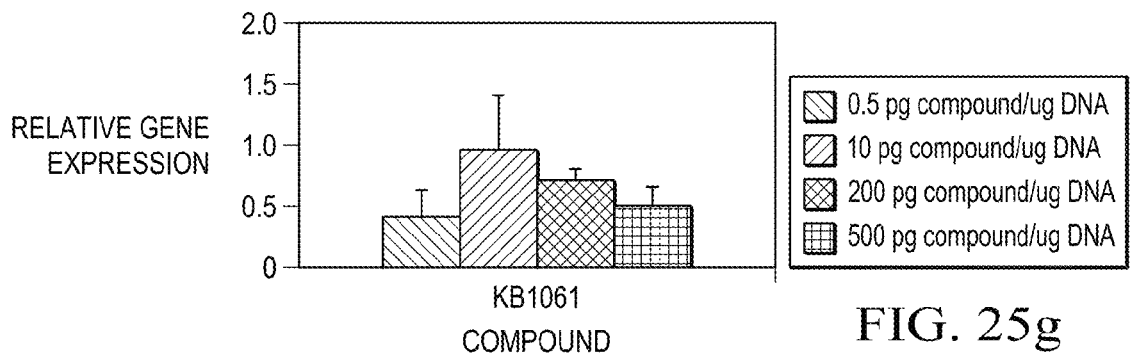
Figure 25H:
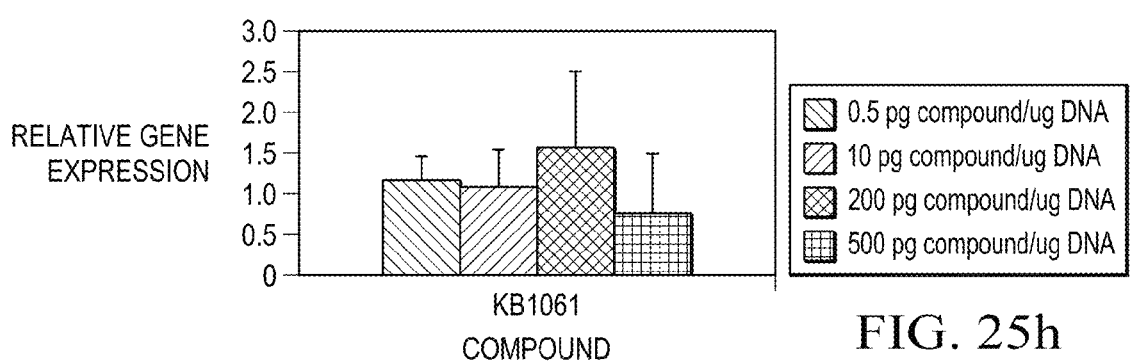

The libraries for small molecule hits were also screened for specific binding to human tumor endothelium for non-small cell lung carcinoma, H1299. A different compound, KB1061, was identified that increased transfection efficiency in H1299 co-cultures (FIG. 25f), but not H1299 cells (FIG. 25g) or HUVEC (FIG. 25h) alone. Ideally, we had planned to identify one ligand that could best mediate delivery to all tumor vascular endothelial cells in our HUVEC+ tumor cell co-cultures. However, due to the known complexity and diversity of different tumor vasculature microenvironments including our co-cultures, our data show that multiple ligands are required to achieve enhanced delivery to the different tumor vasculature phenotypes. Several markers that are specifically expressed on the surface of endothelial cells undergoing angiogenic responses have been identified and used for targeted delivery [23, 36-43] of phage particles, drugs, therapeutic antibodies, and other reagents. Interestingly, gene expression pattern analyses [23, 37] and subtractive proteomic mapping [43] have shown many differences and some similarities in the markers found on the surface of tumor vasculature endothelial cells from different tumor types. In tumor microenvironments, endothelial cells interact with tumor cells, immune cells, pericytes, fibroblasts, pericytes and the extracellular matrix (ECM). Tumor cells can alter the gene expression and phenotype of endothelial cells directly via a paracrine mechanism or indirectly, such as by altering the ECM.

Figure 26A:
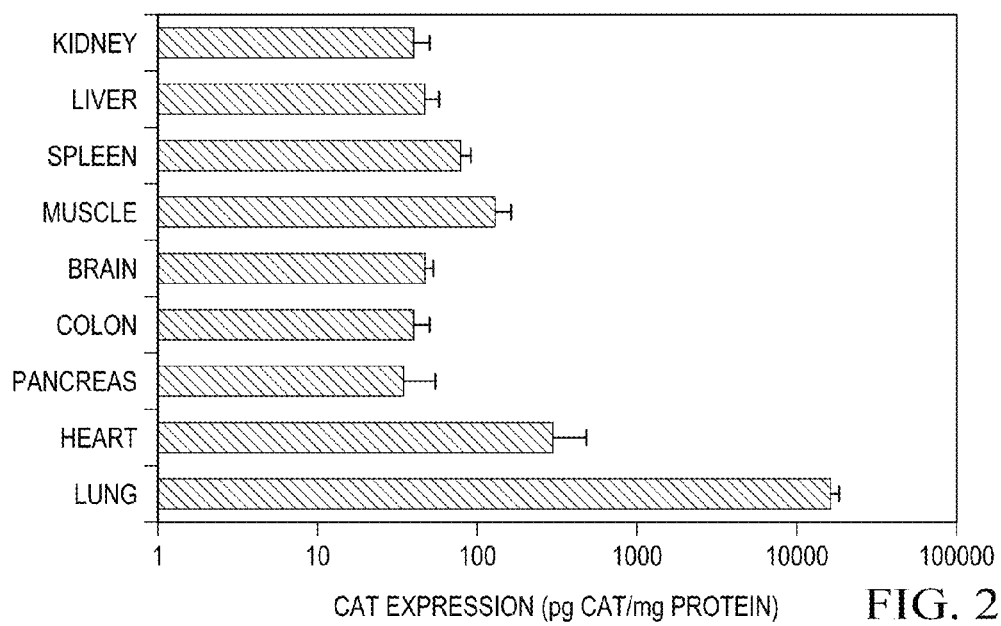
FIGS. 26a to 26c. In vivo targeting and optimization. At 24 h post-IV injections, the majority of KB1023 coated liposomal complexes was transfected non-specifically in the lungs and hearts (a). When injecting using reversible masking (RM), and with increasing RM agent concentration, non-specific uptake by lungs and hearts decreased significantly at 14 h post-IV injections. At 11 mM RM, the lungs and hearts showed little to no non-specific uptake at 14 h post-IV injections (b), while delivery and subsequent gene expression in the tumor tissue increased about 10-fold at 14 h post-IV injections (c). No increased delivery was found in other non-specific tissues, such as liver (c), suggesting that the targeting was specific to the endothelium in the tumor. To dissociate the tumor vascular endothelium from the tumor tissue in order to do the CAT assays and protein assays was prohibitive; therefore, the 10-fold increased delivery to tumor vascular endothelium is a low estimate. Because the tumor endothelium is approximately 5% of the entire tumor volume, the increased targeted delivery to the tumor vasculature is most likely about 200-fold greater than delivery using uncoated BIV complexes alone. Further increasing RM beyond 11 mM did not increase the delivery to tumor tissue and instead diminished delivery and subsequent gene expression. Therefore, for targeted delivery to the tumor endothelium, using 11 mM RM is optimal. #CAT expression was measured 14 h post-IV injection and compared to the control using targeted delivery without RM. *P<0.01. ^P<0.05. N=4~5 per group.

Targeting human tumor endothelium in vivo. The targeting of KB1023 in vivo was confirmed and optimized delivery using reversible masking to bypass non-specific uptake post-intravenous (IV) injection. At 9 days in co-culture, the PANC1 co-cultures were injected intraperitoneally (IP) into SCID mice to establish a human pancreatic tumor endothelium+PANC1 tumor model. Targeted delivery 8 weeks post-IP injections was assessed when pancreatic tumors were about 400 mm$^3$. When KB1023 coated BIV-CAT DNA complexes were IV injected into our PANC-1 co-culture model in SCID mice, the vast majority was delivered to the lungs and hearts non-specifically (FIG. 26a). Only a small portion was delivered to the tumor tissue. This result is consistent with other reports that showed the majority of the DNA:liposome complexes delivered to the lung post-IV injections [15, 45]. A novel "reversible masking" approach was used that produced more efficient than PEGylation for minimizing non-specific delivery while maintaining far higher levels of target cell transfection. To avoid uptake in the lungs and other non-specific target organs, the present invention can also use "shielding/deshielding compounds" that can be added to the complexes used for targeted delivery just prior to injection or administration in vivo (Templeton, N. S. U.S. Pat. No. 7,037,520 B2, relevant portions incorporated herein by reference). The present strategy uses neutral, small molecular weight lipids (about 500 MW and lower), e.g., n-dodecyl- -D-maltopyranoside. Because these lipids are small and not charged, they are loosely associated with the surface of BIV complexes and are removed in the bloodstream by the time they reach the target cell. Overall charge of complexes was measured on a zeta potential analyzer (Delsa 440SX, Beckman-Coulter). BIV complexes 45.5 mV in surface charge transfect cells at the highest levels. Whereas, BIV complexes coated with the reversible masking agent that are 4.8 mV in charge do not transfect cells, tissues or organs (Templeton, N. S., U.S. Pat. No. 7,037,520 B2, relevant portions incorporated herein by reference). Therefore, the overall charge of complexes must be shielded briefly post-injection and then re-exposed when transfecting the target cell.

Figure 26B:
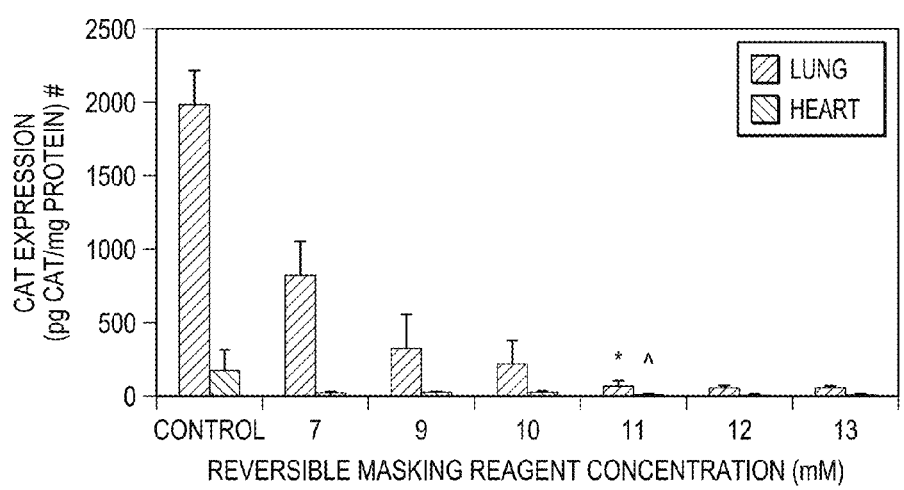

Decreasing the overall charge of BIV complexes was accomplished by adding increasing amounts of reversible masking agent, n-dodecyl- -D-maltopyranoside (Templeton, N. S. U.S. Pat. No. 7,037,520 B2, relevant portions incorporated herein by reference). The reversible mask can be optimized for delivery to a given target organ while bypassing delivery to non-target organs and tissues. FIG. 26b shows that 11 mM n-dodecyl- -D-maltopyranoside (reversible mask) in a 110 μL injection volume was required to bypass delivery of BIV-CAT DNA liposome complexes to lungs and heart post-IV injection (expression reduced by greater than 97%). Correspondingly, delivery of KB1023 coated BIV-CAT DNA complexes+11 mM reversible mask showed approximately 10-fold increased delivery to tumor tissue (FIG. 26c) that included the human tumor vascular endothelium of the PANC-1 co-culture model in SCID mice compared to delivery of uncoated BIV complexes alone (control). To dissociate the tumor vascular endothelium from the tumor tissue in order to perform the CAT assays and protein assays was prohibitive; therefore, the 10-fold increased delivery to tumor vascular endothelium is a low estimate. Because the tumor endothelium is approximately 5% of the entire tumor volume, the increased targeted delivery to the tumor vasculature is most likely about 200-fold greater than delivery using uncoated BIV complexes alone. Our in vivo results, combined with our in vitro data further suggest that KB1023 targeted the tumor endothelial cells and not the cancer cells of the PANC-1 co-culture in SCID mice.

Figure 26C:
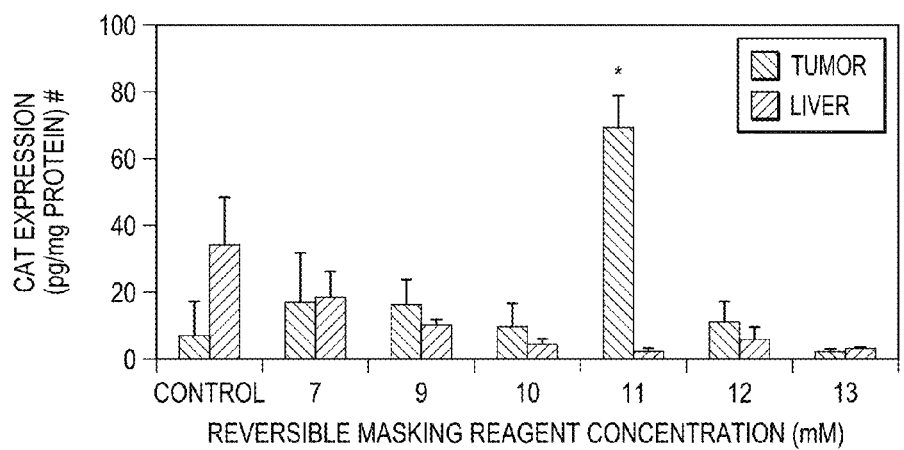

The increased CAT expression obtained with reversible masking was also specific for tumor versus liver. FIG. 26c shows that KB1023 coated BIV-CAT DNA complexes+reversible mask did not increase the CAT expression in liver, and at 11 mM reversible mask expression in the liver was negligible. Therefore, targeting was specific and did not increase uptake and clearance of the complexes by the Kupffer cells in the liver. Further increasing the amount of reversible mask above 11 mM did not result in further increase of CAT expression in the tumors. Instead, the expression decreased showing that 11 mM reversible mask was the optimal concentration to use in the PANC1 co-culture model in SCID mice.

Figure 27:
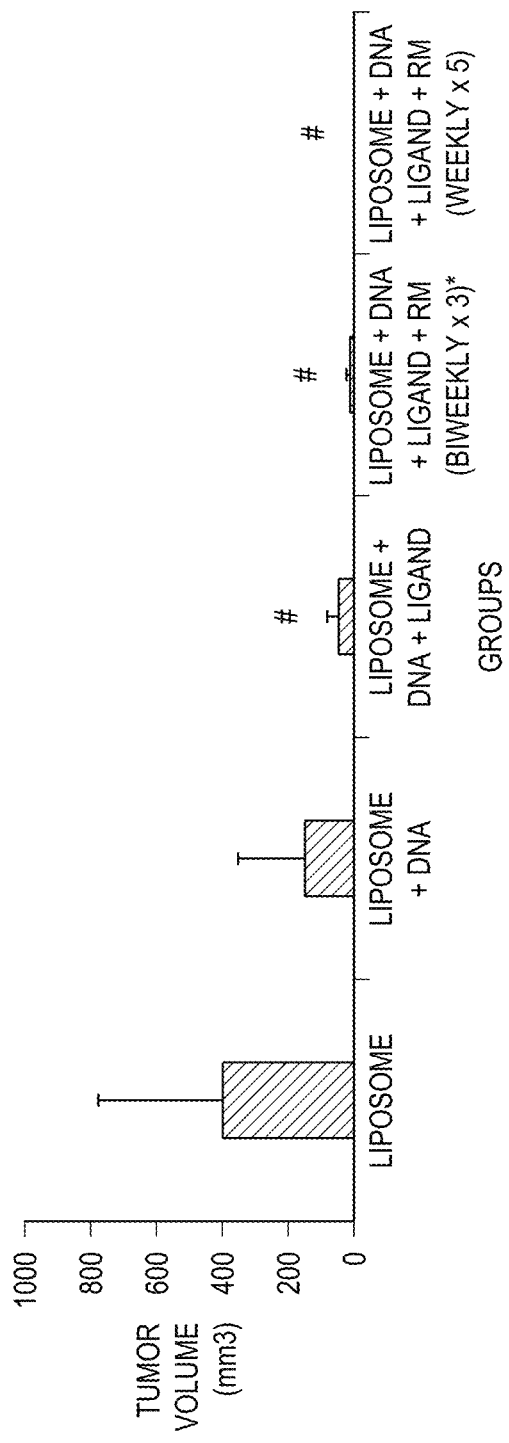
FIG. 27. Tumor growth inhibition using targeted delivery of the TSP1 gene. At 2 weeks post-IP injection of the co-cultures, BIV liposomal complexes that encapsulated 35 μg TSP1 DNA were coated with the ligand KB1023 and co-injected with 11 mM reversible masking (RM) IV into each mouse. The injections were biweekly for a total of three IV injections. At 2 weeks after the final injection (8 weeks post-IP injections of co-cultures), mice were sacrificed to compare intra-abdominal tumor size. Mice treated with human tumor endothelium targeted delivery of TSP1 demonstrated significant cancer growth delay compared to control mice with only liposomes injected. When targeted delivery was combined with optimal reversible masking (RM), tumor growth was suppressed to a greater extent nearly eradicating the tumors. Tumor growth was further suppressed when the treatment was enhanced to weekly injections for a total of five IV injections.*N=20. Other groups have 5~7 mice per group. #P<0.05.

Tumor growth inhibition. After optimizing in vivo targeting using the CAT reporter gene, we tested the efficacy of our targeted delivery in tumor growth prevention using anti-angiogenic TSP1 as the therapeutic gene. FIG. 27 shows the in vivo efficacy data generated after IV injections of BIV-TSP1 DNA complexes with or without the small molecule (ligand), KB1023, and with or without reversible masking (RM) into our human tumor endothelium+PANC-1 tumor bearing mice. As shown in FIG. 27, mice treated with KB1023 coated BIV-TSP1 DNA complexes demonstrated significant suppression of pancreatic cancer growth. Tumor growth was inhibited by 87.99% compared to BIV liposome injection controls (average tumor volume was 47.27 mm$^3$ versus 393.54 mm$^3$). When targeted delivery was combined with reversible masking, tumor growth was inhibited by 98.67% with the average tumor volume of 5.25 mm$^3$ compared to the liposome injected controls at 393.54 mm$^3$. These results were produced after a total of three IV injections administered about once every 2 weeks. Furthermore, when we increased the overall TSP1 therapeutic dosage by increasing the total number of injections to a total of five that were administered once per week, tumor growth was further suppressed and the tumors nearly eliminated (the average tumor volume was 0.7 mm$^3$). Although mice treated with untargeted delivery of TSP1 demonstrated tumor growth retardation by 62.69% with the mean volume of 146.82 mm$^3$, the reduction was not statistically significant (P>0.05). Interestingly, we exceeded the efficacy data reported for TSP1 anti-angiogenic gene therapy approaches using viral vectors, adenovirus [29] or adeno-associated virus [12], cationic polymers [28], or bacterial vectors, *Salmonella choleraesuis* [27]. Presumably, our increased efficacy is attributed to high levels of specific delivery and gene expression exclusively in the human tumor endothelium.

Tumor vasculature is morphologically abnormal, and the vascular endothelial cells differ from normal endothelial cells at molecular and functional levels. Establishing robust and appropriate animal models to understand the biology of the tumor vasculature and to identify anti-angiogenic agents by high-throughput screening is essential for developing the most effective anti-angiogenic cancer therapies. Isolation of tumor endothelial cells from tumor tissue using magnetic beads is a powerful approach to discover tumor endothelial markers, however the cost and low yield of this approach precludes routine study of this tumor endothelium. Another concern is that the tumor endothelial phenotype is lost soon after isolation from the tumor microenvironment. To maintain this important crosstalk between tumor and endothelial cells, an in vitro tumor angiogenesis model was created by co-culturing of lung or pancreatic cancer cells with HUVECs. The present model system provides a robust platform for the discovery of novel anti-angiogenic compounds such as VEGF-A blockers. The model also permits the study of VEGF-A withdrawal and normalization of vasculature because the stimuli from cancer cells can be conveniently removed from the system. In summary, this model provides a simple and feasible way to incorporates the dynamic communication between tumor and endothelial cells. This model was used to successfully identify several tumor endothelium-targeting ligands further supports this concept.

The present invention includes greatly improved specific delivery of BIV liposomes by introducing small ligands that target delivery to tumor endothelium and using reversible masking that provides for bypass of non-specific organs and tissues. Targeted delivery might be possible using small peptides that are multimerized on the surface of liposomes, but these can generate immune responses after repeated injections, particularly systemically, and peptides can preclude penetration and delivery across the interstitial pressure gradient of tumors. Other larger ligands including antibodies, antibody fragments, proteins, partial proteins, etc., are far more refractory than using small peptides for targeted delivery on the surface of liposomes. Our optimized targeted delivery was highly efficient in cancer growth prevention in mouse xenograft models, and the fact that our targeting ligands are small molecules should allow for repeated injections indefinitely without generating immune responses. Additionally, our delivery systems including the ligand (<500 Da) and reversible masking reagent are non-immunogenic and non-toxic, and safe for clinical usage. Moreover, our IV administration once every two weeks or once every week is convenient and could be widely used in medical practice. Therefore, our targeted, reversibly masked delivery system has great potential for effective anti-angiogenic cancer therapy.

As compared to data from other groups who also used liposomes to deliver the TSP1 gene for cancer treatment in human tumor xenograft mouse models [33, 41]. The results presented herein demonstrate significant cancer growth suppression due to our high levels of specific delivery and gene expression exclusively in the human tumor endothelium. Other groups also showed that the combination of p53 and TSP-1 gene therapy synergistically suppressed cancer growth [33, 41]. Combination therapies can also be used with the present invention. Non-viral, viral and bacterial vectors have also been used, including a cationic polymer (Superfect) and several biologically attenuated viral vectors for anti-angiogenic cancer therapy [32, 40-42]. Although they all showed significant cancer growth retardation via local or systemic injection, their efficacy data were not as robust as demonstrated herein (FIG. 27). Direct injection of therapeutics into tumors may be used in some types of primary cancers that are macroscopically visible, e.g. skin cancer, breast cancer. However, this approach is limited and not useful for intra-thoracic, abdominal and other cancers as well as for cancer metastases. IV administration is the most effective delivery route for the treatment of these cancers. Safety is also a concern for viral vectors, particularly when administered systemically. Attenuated viruses are non-pathogenic, however, are still immunogenic and not suitable for repeated injections. A recombinant adeno-associated virus (rAAV)-mediated delivery of antiangiogenic gene therapy in pancreatic cancer therapy was reported by Zhang. However, 4 weeks were required for rAAV-mediated transgenes to reach peak expression levels in circulation after intramuscular or intraportal vein delivery, and the treatment was initiated 4 weeks before the establishment of the tumors [32]. The prolonged delay to reach the therapeutics' steady-state would impose a constraint for its medical application. In contrast, expression of genes using the BIV liposomal delivery system of the present invention, after systemic administration, peaks within 24 h [48] and offers a faster action against cancer growth. Lee et al. demonstrated a significant inhibition of tumor growth for melanoma using *Salmonella* expressing the TSP1 gene. Nevertheless, there was noticeable delivery of the vector to normal tissues (e.g. liver and spleen) which emphasized the need to improve the vector for more specific targeting [40]. Whereas for our targeted, reversibly masked BIV delivery system, the in vivo CAT assay data showed negligible transfection of non-target tissues including liver.

Studies have discovered tumor endothelium marker (TEM) that is uniquely expressed on specific types of tumors as well as several pan-TEMs [23, 37, 49]. Secondly, the potential receptor might be a molecule that is expressed at relatively low levels on normal endothelial cells and up-regulated on some pancreatic tumor endothelial cells. The search for better cell surface receptors to use for targeted delivery is critical and achievable using our approach reported here. Significantly, knowing the function and identity of the best receptors is not required for this targeting strategy. A method developed in the Burgess lab allows production of small molecules designed to bind proteins selectively. Importantly, the bivalent small molecules have both selectivity for binding cell surface receptors, and will resemble secondary structure motifs found at hot-spots in protein-ligand interactions. Bivalent beta-turn mimics were designed that have an affinity for cell surface receptors. Although we did not identify the ligand's receptor to date, we can still use our targeted delivery system in the clinic for anti-angiogenic cancer therapy. In fact, many drugs have been approved by FDA before fully understanding their mechanism. We have reported an extremely effective anti-angiogenic therapeutic approach. Furthermore, our targeted, reversibly masked BIV delivery system using small molecules that target delivery to other diseased target cells could also be applied to the treatment of diseases and disorders other than cancer and metastases.

Cell Culture. PANC1, miaPaCa2, and H1299 cell lines were purchased from the American Type Culture Collection (ATCC, Berthesda, Md.). AsPC-1 and BxPC-3 were generous gifts from Dr. Johnny (Changyi) Chen (Baylor College of Medicine, Houston, Tex.). PANC1 and miaPaCa2 were cultured in high glucose DMEM. AsPC-1, BxPC-3 and H1299 were cultured in RPMI-1640 medium. All the above media were supplemented with 10% fetal bovine serum (FBS), with 2.5% horse serum added to the medium for miaPaCa2 cell growth. HUVEC was purchased from Lonza (Clonetics, Walkersville, Md.) and grown in endothelial basal medium (Clonetics) supplemented with SingleQuots (Clonetics). HUVECs were cultivated at third to sixth passage. Co-culture of HUVECs and cancer cells was established after cell counting and plated at the ratio of approximately 10-30:1 HUVEC: cancer cells with the seeding density of 5,000 HUVECs/cm$^2$. In some experiments, co-cultures were maintained in dual chamber Transwell systems which physically separated cancer cells from ECs while allowing free diffusion between the two cell populations through the 0.4 μm-sized microporous membrane (Corning).

Flow Cytometry. Cells were harvested and resuspended in 1×PBS at 10×10$^6$/ml. The cell suspension was incubated with anti-CD31:RPE (GeneTex, Irvine, Calif.) according to the manufacturer's instructions. After washing, propidium iodide was added to the cell suspension to exclude dead cells in the analysis. Flow cytometry was performed on the BD LSRII (BD Biosciences, San Jose, Calif.) and analyzed by the CellQuest program with gates set on the forward scatter versus the side scatter.

Real-Time Quantitative RT-PCR. Human VEGF-A primers were synthesized containing the following sequences: forward 5'-TGGAATTGGATTCGCCATTT-3' (SEQ ID NO.: 1) and reverse 5'-TGGGTGGGTGTGTCTACAGGA-3' (SEQ ID NO.: 2). β-actin primer sequences were: forward 5'-CTGGAACGGTGAAGGTGACA-3' (SEQ ID NO.: 3) and reverse 5'-AAGGGACTTCCTGTAACAATGCA-3' (SEQ ID NO.: 4). Co-cultured cells were grown in transwell plates. Total RNA was extracted from the cells using Trizol (Invitrogen, Carlsbad, Calif.) following the manufacturer's protocol and treated with DNase I (Invitrogen). One µg of total RNA was reverse-transcribed into cDNAs with an iScript cDNA synthesis kit (Bio-Rad, Hercules, Calif.) containing a mixture of oligo(dT) and random primers. Real-time PCR was performed on an ABI PRISM 7900HT Sequence Detection System (Applied Biosystems, Foster City, Calif.) using a DyNAmo HS SYBR Green qPCR kit (New England BioLabs, Finnzymes, Finland). Cycling conditions were the following: initial denaturation at 95° C. for 10 min, followed by 40 cycles at 95° C. for 15 s and 60° C. for 1 min.

Western Blot. Eight days after co-culture in transwell dishes, 50 mg protein from EC lysates was loaded on 9% SDS-PAGE gels followed by Western transfer to nitrocellulose membranes (Hybond ECL; Amersham Pharmacia Biotech). The membranes were blocked with 5% nonfat milk in TBS (20 mM Tris-HCl, 150 mM NaCl [pH 7.4], and 0.05% Tween 20). After incubation with the primary human anti-VEGF antibody (R&D Systems, Minneapolis, Minn.) at 1 µg/mL for 2 h at room temperature (RT), the membranes were washed six times at 5-min intervals with TBS/0.05% Tween 20 and incubated with secondary anti-goat horseradish peroxidase-conjugated antibody (Transduction Laboratories, Lexington, Ky.) [50].

Tube Formation Assay. Eight days after co-culture in transwell plates, Matrigel (BD Biosciences, San Jose, Calif.) was added to the receiver chamber of a blank 6-well transwell plate at 4° C. and incubated for 2 h at 37° C. After Matrigel had solidified, endothelial cells were trypsinized, counted and seeded on top at $5\times10^5$ cells/well. Cells were incubated for 16 h to allow the formation of capillary-like structures. To maintain the co-culture conditions, the cancer cells were cultivated in the upper chamber of the transwell plate. The tubular structure was observed daily to monitor morphology, integrity survival.

Preparation of BIV DNA:Liposome Complexes. Plasmids p4241 and p4119 were generous gifts from Robert Debs (California Pacific Medical Center Research Institute, San Francisco, Calif.). They encode the luciferase and CAT genes, respectively. pCMV-THBS-1 was a kind gift from David Roberts (National Institutes of Health, Bethesda, Md.) and encodes the TSP1 gene. All plasmids were grown under ampicillin selection in DH5a *Escherichia coli*. Plasmid DNA was purified by anion exchange chromatography using the Qiagen Endo-Free Plasmid Giga Kit (Qiagen, Hilden Germany). DOTAP and DOTAP:Chol BIV liposomes, BIV DNA:liposome complexes (BIV complexes) were prepared as previously described [15], except that synthetic cholesterol (Sigma-Aldrich, St. Louis, Mo.) was used at a ratio of 50:45 DOTAP:cholesterol.

Bivalent Small Molecule Production. Briefly, through selective coupling the β-turn monovalent small molecules were mixed in solution to produce homodimer, KB991-KB1005, and heterodimer, KB1006-KB 1140 bivalent small molecules. During the process, only potassium carbonate was required to affect the coupling. Boc-protected monomeric compounds were treated with 30% TFA in $CH_2Cl_2$ for 4 h at 25° C. The solvent was removed and residue was re-dissolved in DMSO to make a solution of 0.03 M. The dichlorotriazine linker scaffold and $K_2CO_3$ were sequentially added. The resulting suspension was sonicated for 15 min and rocked for 7 days. DMSO was lyophilized, and aqueous HCl solution (5%, about 0.5 mL) was added to the above solid residue and sonicated for 3 min. Most of the compounds were precipitated in acidic solutions. After centrifugation, the pellets were dried and saved. In order to coat the monovalent or bivalent small molecules onto the surface of BIV complexes, a hydrocarbon tail was included in the molecules for insertion into the surface lipid bilayer. Compounds (about 10.0 mg) were initially dissolved in 1.0 mL THF/$H_2O$ (v:v=1:1). $CuSO_4$ solution (1.0 M, 10 µL) was added and followed by Cu powder (1.0 mg). After that procedure, azidooctadecane in THF solution (0.1 mmol, 0.2 mL) was added, and the resulting suspension was stirred at 25° C. for 24 h. The suspension was filtered through a glass pipette filled with silica gel using 30% methanol in $CH_2Cl_2$ as eluents. The solution was dried and concentrated to the final products. After synthesis, the solid compounds were dissolved in 1:1 chloroform:methanol in glass test tubes. Thin films were produced at the bottom of the tubes under a steady stream of argon gas under the tissue culture hood. The films were dissolved in sterile water to produce a 5 mg/mL stock and subjected to sonication (Lab-Line Trans-sonic 820/H) at 50° C. Aliquots of the reconstituted compounds were stored at −80° C.

In Vitro Delivery and High Throughput Luciferase Assay. The high throughput assay of the present invention was used to identify monovalent or bivalent compounds attached to the surface of BIV complexes that internalize into tumor vascular endothelial cells more efficiently than non-targeted BIV complexes. The assay features a luciferase reporter gene and a dedicated plate reader luminometer, the Luminoskan Ascent, which is certified for ultra-sensitive detection of luciferase expression (Thermo Electron Corp., Waltham, Mass.) that has 3 injectors/robotic dispensers. The Luminoskan is versatile insofar as it allows many different sample formats from single 10 cm tissue culture dishes to 384-well plates, all of which can be analyzed either from the top or the bottom of the sample. It offers an extremely high degree of sensitivity (<1 fmol ATP/well) for observing small differences in addition to a high dynamic range for samples (>9 decades over whole gain setting area). The Luminoskan provides accurate data by allowing optimal control of assay conditions including temperature (the amount of light emitted is very sensitive to small changes), adequate mixing of reagents (orbital shaking feature), a constant delay between each measurement, and other features such as allowing multiple replicates per sample (30/well and up to 3500/culture dish). Finally, the Luminoskan Ascent software is designed well for data management. If the plasmid DNA encoding luciferase is internalized and efficiently transported to the nucleus, then bioluminescence is detected in cells grown in the wells of the plates. The read out is fast, enabling rapid testing of functionalized BIV complexes in a one-bivalent compound-per-well format. Normal HUVECs were used for controls, and delivery to the tumor cells alone or to the co-cultures was compared. Luminoskan data was used to identify the bivalent compounds that produce the highest levels of luciferase gene expression in HUVECs that are co-cultured with human tumor cells and not in normal HUVEC cells or in the tumor cells. Approximately 150 members of the small molecule library were tested at various concentrations on the surface of BIV-luciferase complexes. Optimal transfection time, amount of complexes used for transfection, the optimal integration and lag time were also determined.

Briefly, 7 days after co-culture, cells were harvested and 50 μL cell suspension was seeded to 96-well dishes at $2 \times 10^4$ cells/well. Complexes were prepared as previously described [15]. The compounds were diluted to concentrations including 0.5, 10, 200, 500 pg compound/μg DNA encapsulated in the complexes. 1 μL of compound was pipeted slowly into the center of 10 μL of BIV-luciferase DNA complexes that were pre-loaded in 96-well plates and followed by incubation at RT overnight for maximal coating. The following day, cells were transfected with 0.52 μL compound-coated BIV complexes which was diluted to 5 μL and placed into 45 μL serum free medium. Cells were grown in cell culture medium post-transfection. For co-cultures of HUVEC with H1299 cells, DOTAP BIV liposomes were used, and cells were transfected for 4 h. For co-cultures of HUVEC and PANC1 cells, DOTAP:Chol BIV liposomes were used, and cells were transfected for 2 h. At 24 h post-transfection, cells were lysed using 1% Triton X-100 (Sigma-Aldrich, St. Louis, Mo.) followed by high throughput luciferase assay using the Luminoskan Ascent to detect gene expression. 1 sec of integration time and 14 sec of lag time were applied during the assay. Transfection efficiencies of the compound coated BIV liposomal complexes were compared to that of uncoated complexes. Triplicates were measured for each condition. All the dilutions were made in 5% dextrose in water (D5W).

Human Tumor Endothelium-Pancreatic Cancer Mouse Model. HUVEC and PANC1 co-cultured cells were harvested and resuspended in 1×PBS after 8 days in co-culture. A 500 μL cell suspension containing $2 \times 10^6$ co-cultured cells (about $1 \times 10^6$ PANC1 cells) was IP injected into each 8~10 week-old severe combined immunodeficient (SCID) mouse. All animal procedures were performed in accordance with the Baylor College of Medicine (Houston, Tex.) institutional guidelines using an approved animal protocol.

In Vivo Targeted Delivery and CAT Assay. At 8 weeks post-IP injections of co-cultures detailed above, BIV-CAT DNA complexes were prepared and coated with the small molecule KB1023 at 500 pg compound/μg DNA as discussed above. The complexes were mixed with various concentrations of reversible masking reagent, n-dodecyl- -D-maltopyranoside (Anatrace, Maumee, Ohio), just prior to intravenous (IV) injections into mice. Each mouse was injected with a total volume of 110 μL complexes containing 50 μg of p4119 CAT DNA. At 14 h post-IV injection, mice were sacrificed, tissues were harvested, and total protein was extracted as previously described [15]. CAT protein production was measured using the CAT ELISA kit (Roche, Indianapolis, Ind.) following the manufacturer's instructions. Protein concentration was determined using the Micro BCA kit (Pierce) following the manufacturer's instructions.

Anti-Angiogenic Cancer Therapy. At 2 weeks post-IP injections of the co-cultures detailed above, in vivo delivery was performed using the protocol described above, except that 35 μg TSP1 plasmid DNA was encapsulated in the BIV-KB1023 coated complexes and 11 mM reversible masking reagent was used prior to IV injections. Injections were performed biweekly for a total of three injections. In a different experimental group, injections were performed weekly for a total of five injections. Two weeks after the final injection (8 weeks post-IP injection of the co-cultures to establish the tumor model), the mice were sacrificed and tumor size was measured. Intra-abdominal tumors and other organs (liver, lungs, spleen, pancreas and colon) were dissected followed by fixation in 10% neutral buffered formalin.

Statistical Analysis. Data were expressed as means±SEM. Experimental and control groups were compared using the unpaired student t test. P<0.05 was considered significant.

The SK-MEL-28 cells are a melanoma cell line obtained from the ATCC (American Type Culture Collection, Manassas, Va.). Abdominal wall melanoma tumor cells and left gluteal melanoma tumor cells were provided by a surgeon at Medical City, Dallas, Tex., samples of which are at Gradalis, Inc. Dallas, Tex. The patient tissue was first dissociated by collagenase and pulmozyme followed by using a tissue dissociator using standard procedures in accordance with the manufacturer's instructions (Miltenyl Biotec, Bergisch Gladbach, Germany). SK-MEL-28 cells were grown according to ATCC's specified conditions. Patient cells were passaged once per week and assayed after the ninth passage. All cells were grown in DMEM (Dulbecco's Modified Eagle's Medium) supplemented with 10% fetal bovine serum. All other conditions are as found herein above.

Figure 28:
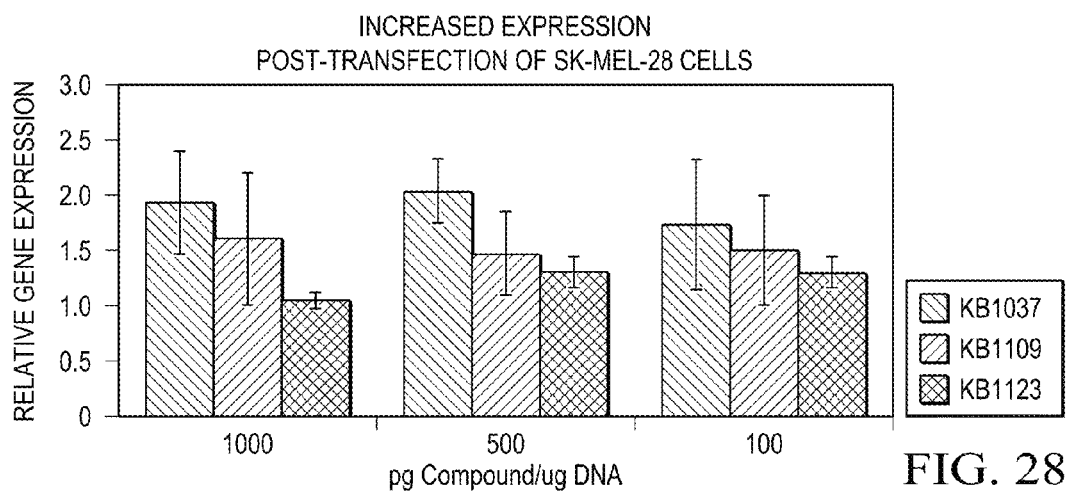
FIG. 28 shows the increased expression post-transfection of SK-MEL-28 cells with KB1037, KB1109 and KB1123.
Figure 29:
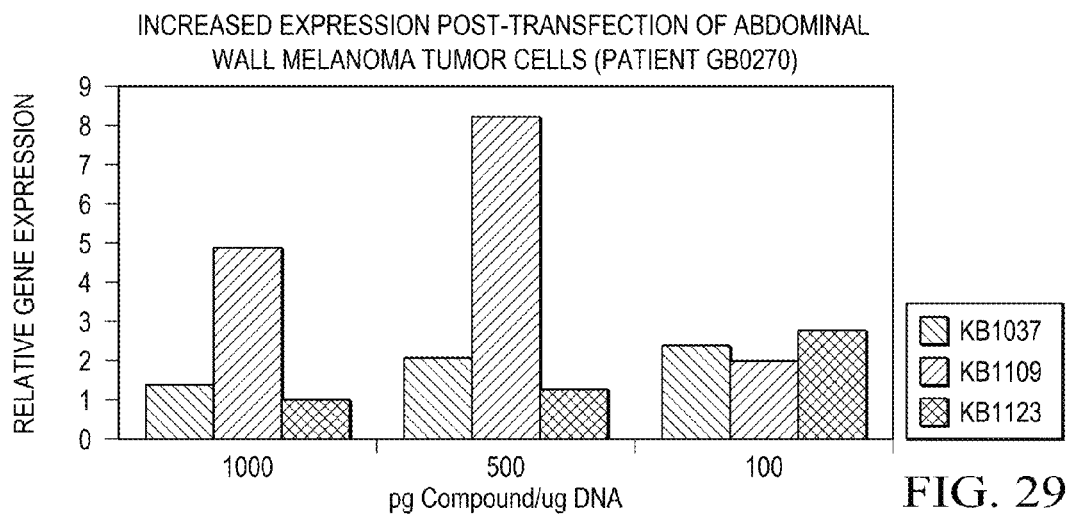
FIG. 29 shows the increased expression post-transfection of abdominal wall melanoma tumor cells with KB1037, KB1109 and KB1123.
Figure 30:
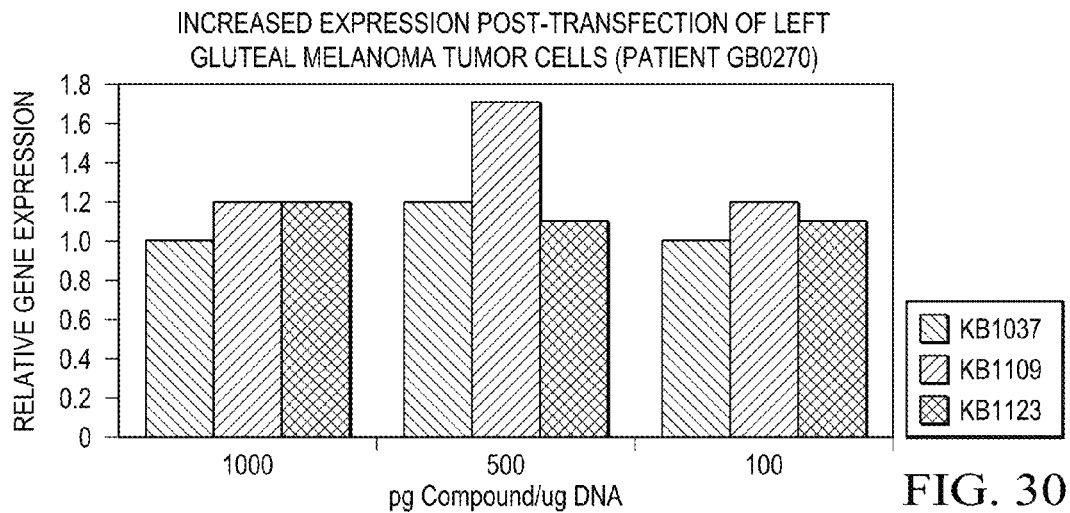
FIG. 30 shows the increased expression post-transfection of left gluteal melanoma tumor cells with KB1037, KB1109 and KB1123.

FIG. 28 shows the increased expression post-transfection of SK-MEL-28 cells with KB1037, KB1109 and KB1123. FIG. 29 shows the increased expression post-transfection of abdominal wall melanoma tumor cells with KB1037, KB1109 and KB1123. FIG. 30 shows the increased expression post-transfection of left gluteal melanoma tumor cells with KB1037, KB1109 and KB1123. It was found that KB1109 significantly increased expression on melanoma cells from all sources. KB1037 and KB1123 increased expression on SK-MEL-28 and melanoma cells from the abdominal wall of Patient GB0270.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Reference numbers in bold throughout the Detailed Description correspond to the original numbering in the grant and the paper, respectively. The numbering in italics is the numbering used in the patent application. The following numbering is the corrected numbering.

1. Improved DNA: liposome complexes for increased systemic delivery and gene expression, N. S. Templeton, D. D. Lasic, P. M. Frederik, H. H. Strey, D. D. Roberts, and G. N. Pavlakis, Nature Biotechnology, 1997, 15, 647-652.
2. Liposomal delivery of nucleic acids in vivo, N. S. Templeton, DNA and Cell Biology, 2002, 21, 857-867.
3. Successful treatment of primary and disseminated human lung cancers by systemic delivery of tumor suppressor genes using an improved liposome vector, R. Ramesh, T. Saeki, N. S. Templeton, L. Ji, L. C. Stephens, I. Ito, D. R. Wilson, Z. Wu, C. D. Branch, J. D. Minna, and J. A. Roth, Molecular Therapy, 2001, 3, 337-350.
4. Openings between defective endothelial cells explain tumor vessel leakiness, H. Hashizume, P. Baluk, S. Morikawa, J. W. McLean, G. Thurston, S. Roberge, R. K. Jain, and D. M. McDonald, Am J Pathol, 2000, 156, 1363-1380.
5. Effect of transvascular fluid exchange on pressure-flow relationship in tumors: a proposed mechanism for tumor blood flow heterogeneity, P. A. Netti, S. Roberge, Y. Boucher, L. T. Baxter, and R. K. Jain, Microvasc Res, 1996, 52, 27-46.
6. Vascular permeability and microencapsulation of gliomas and mammary carcinomas transplanted in rat and mouse cranial windows, F. Yuan, H. A. Salehi, Y. Boucher, U.S. Vasthare, R. F. Tuma, and R. K. Jain, Cancer Res, 1994, 54, 4564-4568.
7. Vasculogenic mimicry, R. Folberg, and A. J. Maniotis, APMIS, 2004, 112, 508-525.
8. Remodeling of the microenvironment by I melanoma tumor cells, M. J. Hendrix, E. A. Seftor, D. A. Kirschmann, V. Quaranta, and R. E. Seftor, Ann N Y Acad Sci, 2003, 995, 151-161.
9. Discovering High-Affinity Ligands for Proteins: SAR by NMR, S. B. Shuker, P. J. Hajduk, R. P. Meadows, and S. W. Fesik, Science, 1996, 274, 1531-1534.
10. Discovery of Potent Nonpeptide Inhibitors of Stromelysin Using SAR by NMR, P. J. Hajduk, G. Sheppard, D. G. Nettesheim, E. T. Olejniczak, S. B. Shuker, R. P. Meadows, D. H. Steinman, G. M. Carrera, P. A. Marcotte, J. Severin, K. Walter, H. Smith, E. Gubbins, R. Simmer, T. F. Holzman, D. W. Morgan, S. K. Davidsen, J. B. Summers, and S. W. Fesik, J. Am. Chem. Soc., 1997, 119, 5818-5827.
11. One-Dimensional Relaxation- and Diffusion-Edited NMR Methods for Screening Compounds That Bind to Macromolecules, P. J. Hajduk, E. T. Olejniczack, and S. W. Fesik, J. Am. Chem. Soc., 1997, 119, 12257-12261.
12. NMR-Based Discovery of Lead Inhibitors That Block DNA Binding of the Human Papillomavirus E2 Protein, P. J. Hajduk, J. Dinges, G. F. Miknis, M. Merlock, T. Middleton, D. J. Kempf, D. A. Egan, K. A. Walter, T. S. Robins, S. B. Shuker, T. F. Holzman, and S. W. Fesik, J. Med. Chem, 1997, 40, 3144-3150.
13. Structure-Activity Relationships by NMR: A New Procedure for Drug Discovery by a Combinatorial-Rational Approach, H. Kessler, Angew. Chem. Int. Ed., 1997, 36, 829-831.
14. Stromelysin Inhibitors Designed from Weakly Bound Fragments: Effects of Linking and Cooperativity, E. T. Olejniczak, P. J. Janduk, P. A. Marcotte, D. G. Nettesheim, R. P. Meadows, R. Edalji, T. F. Holzman, and S. W. Fesik, J. Am. Chem. Soc., 1997, 119, 5828-5832.
15. Identification of a Small Molecule Inhibitor of the IL-2/IL-2Ra Receptor Interaction Which Binds to IL-2, J. W. Tilley, L. Chen, D. C. Fry, S. D. Emerson, G. D. Powers, D. Biondi, T. Varnell, R. Trilles, R. Guthrie, F. Mennona, G. Kaplan, R. A. LeMahieu, R. Palermo, and G. Ju, J. Am. Chem. Soc., 1997, 119, 7589-7590.
16. The SHAPES strategy: an NMR-based approach for lead generation in drug discovery, J. Fejzo, C. A. Lepre, J. W. Peng, G. W. Bemis, Ajay, M. A. Murcko, and J. M. Moore, Chem. Biol., 1999, 5, 755-769.
17. Privileged Molecules for Protein Binding Identified from NMR-Based Screening, P. J. Hajduk, M. Bures, J. Praestgaard, and S. W. Fesik, J. Med. Chem., 2000, 43, 3443-3447.
18. SNAr Cyclizations to Form Cyclic Peptidomimetics of b-Turns, Y. Feng, Z. Wang, S. Jin, and K. Burgess, J. Am. Chem. Soc., 1998, 120, 10768-10769.

19. Solid Phase SNAr Macrocyclizations to Give Turn-extended-turn Peptidomimetics, Y. Feng, and K. Burgess, Chem. Eur. J., 1999, 5, 3261-3272.
20. Conformations of Peptidomimetics Formed by SNAr Macrocyclizations: 13- to 16-Membered Ring Systems, Y. Feng, Z. Wang, S. Jin, and K. Burgess, Chem. Eur. J., 1999, 5, 3273-3278.
21. Stereochemical Implications of Diversity in b-Turn Peptidomimetic Libraries, Y. Feng, M. Pattarawarapan, Z. Wang, and K. Burgess, J. Org. Chem., 1999, 64, 9175-9177.
22. Facile Macrocyclizations to b-Turn Mimics with Diverse Structural, Physical, and Conformational Properties, C. Park, and K. Burgess, J. Comb. Chem., 2001, 3, 257-266.
23. A New Solid-Phase Linker for Suzuki Coupling with Concomitant Macrocyclization: Synthesis of b-Turn Mimics, W. Li, and K. Burgess, Tetrahedron Lett., 1999, 40, 6527-6530.
24. Preferred Secondary Structures as a Possible Driving Force for Macrocyclization, S. Reyes, M. Pattarawarapan, S. Roy, and K. Burgess, Tetrahedron, 2000, 56, 9809-9818.
25. Solid-Phase Syntheses of b-Turn Analogues To Mimic or Disrupt Protein-Protein Interactions, K. Burgess, Acc. Chem. Res., 2001, 34, 826-835.
25. Long-Lasting Rescue of Age-Associated Deficits in Cognition and the CNS Cholinergic Phenotype by a Partial Agonist Peptidomimetic Ligand of TrkA, M. A. Bruno, P. B. S. Clarke, A. Seltzer, R. Quirion, K. Burgess, A. C. Cuello, and H. U. Saragovi, J. Neuroscience, 2004, 24, 8009-8018.
26. Folkman, J, and Kalluri, R (2004). Cancer without disease. Nature 427: 787.
27. Tandle, A, Blazer, D G, 3rd, and Libutti, S K (2004). Antiangiogenic gene therapy of cancer: recent developments. J Transl Med 2: 22.
28. Ferrara, N, Hillan, K J, Gerber, H P, and Novotny, W (2004). Discovery and development of bevacizumab, an anti-VEGF antibody for treating cancer. Nat Rev Drug Discov 3:391-400.
29. Faivre, S, Demetri, G, Sargent, W, and Raymond, E (2007). Molecular basis for sunitinib efficacy and future clinical development. Nat Rev Drug Discov 6: 734-745.
30. Templeton, N S (ed) (2008). Gene and Cell Therapy: Therapeutic Mechanisms and Strategies. CRC Press: Boca Raton, Fla. 1101 p.
31. Ramesh, R, et al. (2001). Successful treatment of primary and disseminated human lung cancers by systemic delivery of tumor suppressor genes using an improved liposome vector. Mol Ther 3: 337-350.
32. Zhang, X, Xu, J, Lawler, J, Terwilliger, E, and Parangi, S (2007). Adeno-associated virus-mediated antiangiogenic gene therapy with thrombospondin-1 type 1 repeats and endostatin. Clin Cancer Res 13: 3968-3976.
33. Xu, M, Kumar, D, Stass, S A, and Mixson, A J (1998). Gene therapy with p53 and a fragment of thrombospondin I inhibits human breast cancer in vivo. Mol Genet Metab 63: 103-109.
34. Liu, S, et al. (2008). PDX-1 acts as a potential molecular target for treatment of human pancreatic cancer. Pancreas 37: 210-220.
35. Park, C, and Burgess, K (2001). Facile macrocyclizations to beta-turn mimics with diverse structural, physical, and conformational properties. J Comb Chem 3: 257-266.
36. Reyes, S, Pattarawarapan, M, Roy, S, and Burgess, K (2000). Preferred secondary structures as a possible driving force for macrocyclization. Tetrahedron 56: 9809-9818.
37. Burgess, K (2001). Solid-phase syntheses of beta-turn analogues to mimic or disrupt protein-protein interactions. Acc Chem Res 34: 826-835.
38. Bruno, M A, et al. (2004). Long-lasting rescue of age-associated deficits in cognition and the CNS cholinergic phenotype by a partial agonist peptidomimetic ligand of TrkA. J Neurosci 24: 8009-8018.
39. Isenberg, J S, Martin-Manso, G, Maxhimer, J B, and Roberts, D D (2009). Regulation of nitric oxide signalling by thrombospondin 1: implications for anti-angiogenic therapies. Nat Rev Cancer 9: 182-194.
40. Lee, C H, Wu, C L, and Shiau, A L (2005). Systemic administration of attenuated *Salmonella* choleraesuis carrying thrombospondin-1 gene leads to tumor-specific transgene expression, delayed tumor growth and prolonged survival in the murine melanoma model. Cancer Gene Ther 12: 175-184.
41. Xu, M, Chen, Q R, Kumar, D, Stass, S A, and Mixson, A J (1998). In vivo gene therapy with a cationic polymer markedly enhances the antitumor activity of antiangiogenic genes. Mol Genet Metab 64: 193-197.
42. Liu, P, et al. (2003). Adenovirus-mediated gene therapy with an antiangiogenic fragment of thrombospondin-1 inhibits human leukemia xenograft growth in nude mice. Leuk Res 27: 701-708.
43. Templeton, N S, Lasic, D D, Frederik, P M, Strey, H H, Roberts, D D, and Pavlakis, G N (1997). Improved DNA: liposome complexes for increased systemic delivery and gene expression. Nat Biotechnol 15: 647-652.
44. Kerbel, R S (2008). Tumor angiogenesis. N Engl J Med 358: 2039-2049.
45. Angell, Y, Chen, D, Brahimi, F, Saragovi, H U, and Burgess, K (2008). A combinatorial method for solution-phase synthesis of labeled bivalent beta-turn mimics. J Am Chem Soc 130: 556-565.
46. Maliartchouk, S, et al. (2000). A designed peptidomimetic agonistic ligand of TrkA nerve growth factor receptors. Mol Pharmacol 57: 385-391.
47. Thurston, G, et al. (1998). Cationic liposomes target angiogenic endothelial cells in tumors and chronic inflammation in mice. J Clin Invest 101: 1401-1413.
48. Lu, H, Zhang, Y, Roberts, D D, Osborne, C K, and Templeton, N S (2002). Enhanced gene expression in breast cancer cells in vitro and tumors in vivo. Mol Ther 6: 783-792.

What is claimed is:

1. A tissue-specific targeting ligand for targeted delivery of therapeutic agents to a tissue comprising:

a composition of formula:

A-scaffold-A', wherein the scaffold is of the formula:

(a)

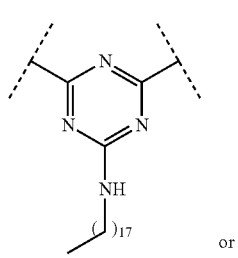

or (b)

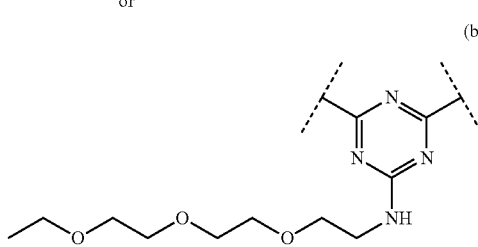

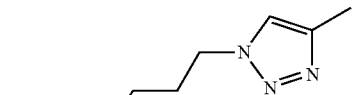

wherein the dotted lines represent the point of attachment to A and A';

wherein A and A' comprise monovalent peptidomimetic compounds, wherein each monovalent peptidomimetic compound has the following formula:

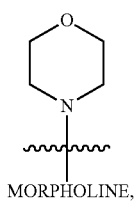

MORPHOLINE, wherein the composition is incorporated into a lipid bilayer.

2. The targeted ligand of claim 1, wherein the tissue is a cancerous cell, tissue or endothelium selected from pancreatic cancer, breast cancer, non-small cell lung carcinoma (NSCLC), pancreatic cancer vascular endothelium or NSCLC cancer vascular endothelium.

3. A method for synthesizing a small molecule complex for targeted delivery of therapeutic agents to a tissue, the method comprising:
coupling covalently two or more unprotected monovalent peptidomimetic compounds, of formulas A and A', to a scaffold, wherein the scaffold is of the formula:

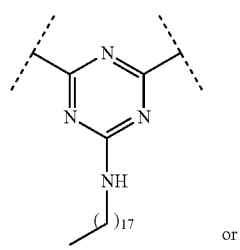

or wherein the dotted lines represent the point of attachment to A and A':
wherein A and A' comprise monovalent peptidomimetic compounds, wherein each monovalent peptidomimetic compound has the following formula:

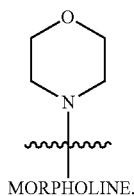

MORPHOLINE.

4. The method of claim 3, wherein the tissue is a cancerous cell, tissue or endothelium selected from pancreatic cancer, breast cancer, non-small cell lung carcinoma (NSCLC), pancreatic cancer vascular endothelium or NSCLC cancer vascular endothelium.

5. A ligand-functionalized delivery system comprising:
a therapeutic agent carrier;
a tissue-specific targeting ligand for targeted delivery of therapeutic agents to a tissue comprising:

(a)

(b)

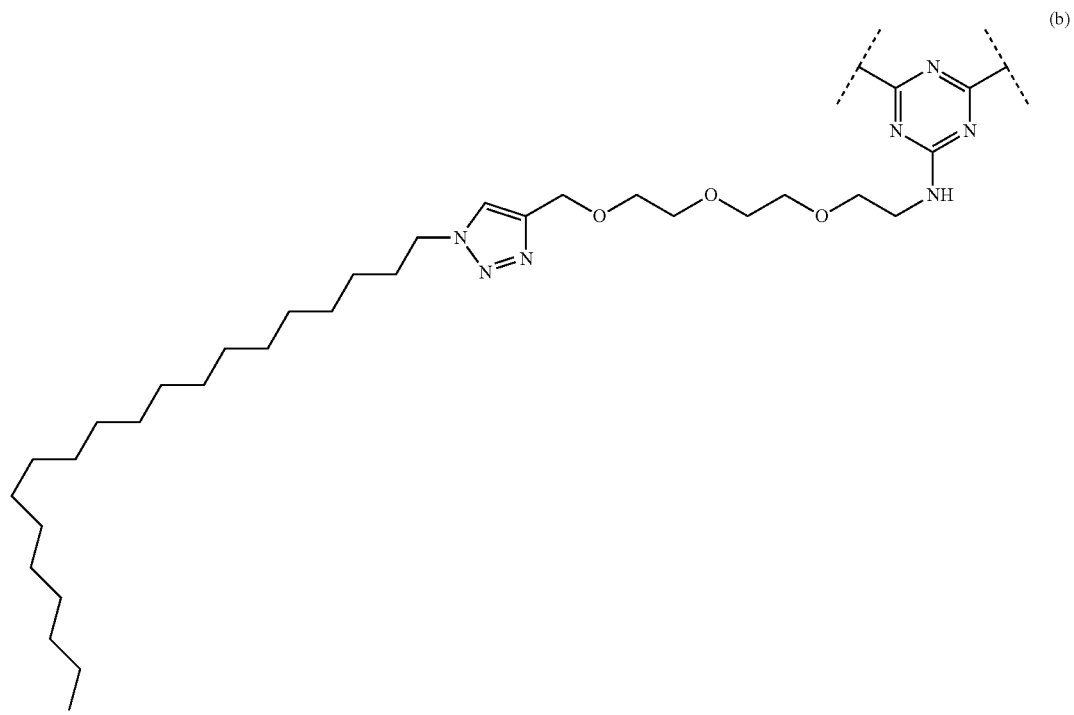

a composition of formula:
A-scaffold-A',
wherein the scaffold is of the formula:

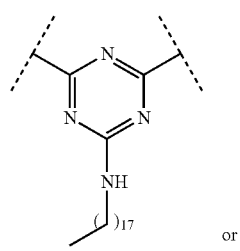

(a)

or

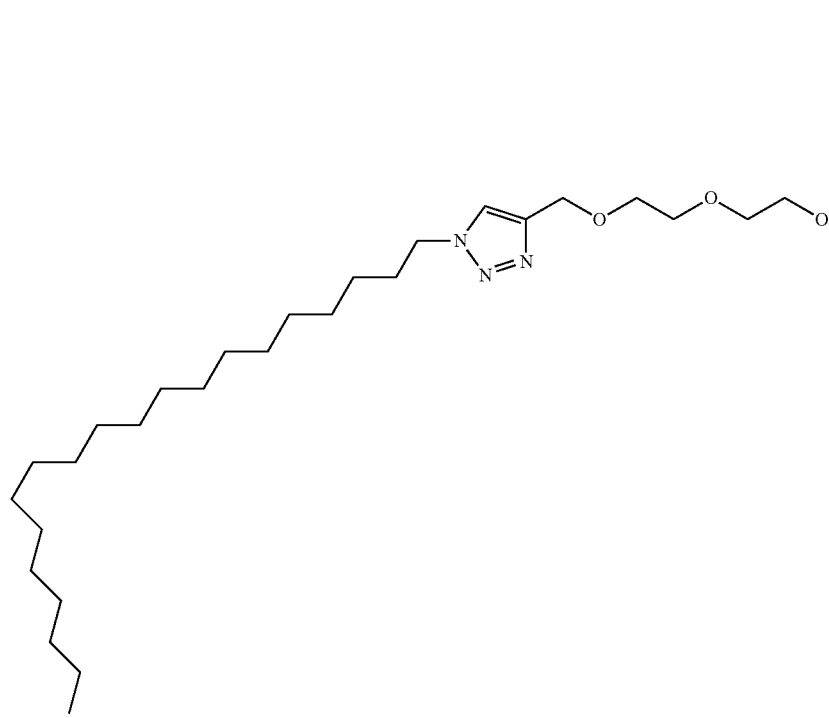

(b)

wherein the dotted lines represent the point of attachment to A and A':

wherein A and A' comprise monovalent peptidomimetic compounds, wherein each monovalent peptidomimetic compound has the following formula:

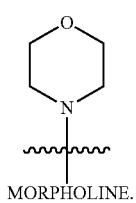

MORPHOLINE.

6. The ligand-functionalized delivery system of claim 5, wherein the therapeutic agent carrier is a liposome.

7. The ligand-functionalized delivery system of claim 5, wherein the therapeutic agent carrier is a cationic liposome having an internal lipid bilayer and an external lipid bilayer.

8. The ligand-functionalized delivery system of claim 5, wherein the tissue is a cancerous cell, tissue or endothelium selected from pancreatic cancer, breast cancer, non-small cell lung carcinoma (NSCLC), pancreatic cancer vascular endothelium or NSCLC cancer vascular endothelium.

9. A method of delivering a payload to a target tissue comprising the steps of:

preparing a composition of formula:
A-scaffold-A',
wherein the scaffold is of the formula:

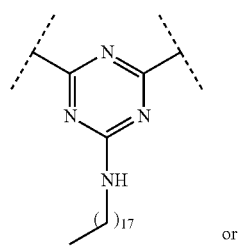

(a)

or

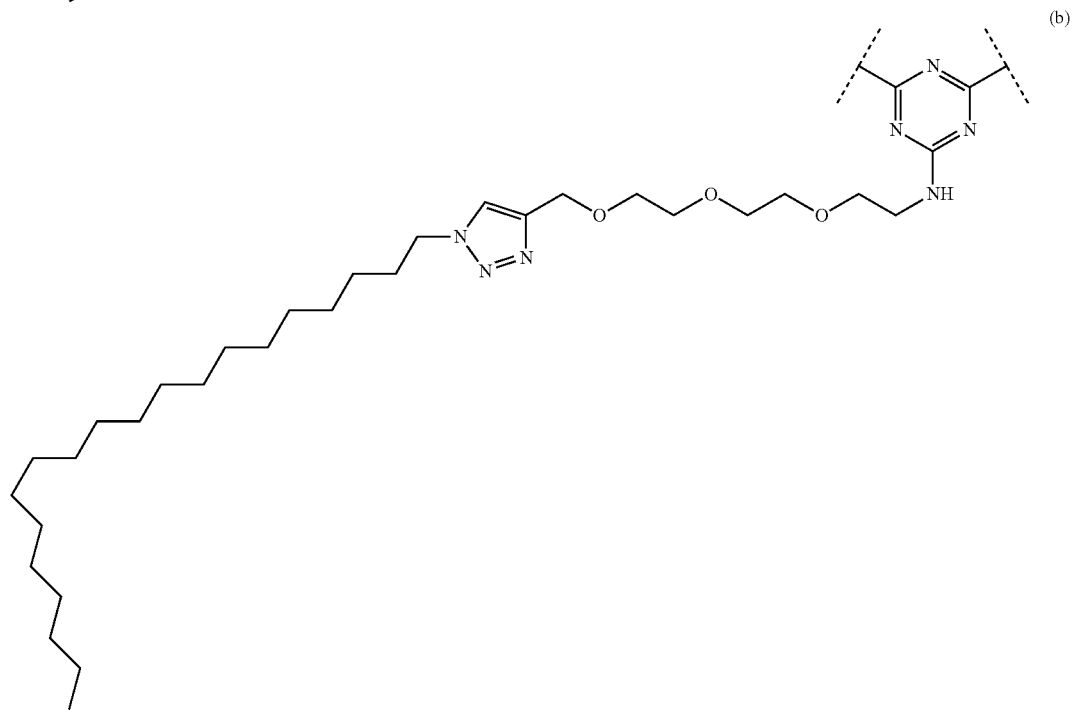

(b)

wherein the dotted lines represent the point of attachment to A and A':
wherein A and A' comprise monovalent peptidomimetic compounds, wherein each monovalent peptidomimetic compound has the following formula:

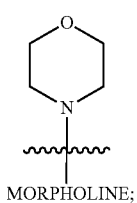

MORPHOLINE;

incorporating the composition into a liposome that encapsulates a therapeutic agent to form a targeted liposome complex;
combining the targeted liposome complex with a reversible masking reagent; and
administering a therapeutically effective amount of the masked targeted liposome complex to a patient in need thereof.

10. The method of claim 9, wherein the liposome is a bilamellar invaginated vesicle.

11. The method of claim 9, wherein the reversible masking agent is a small neutral lipid with a molecular weight of about 500 Da or lower.

12. The method of claim 11, wherein the small neutral lipid is n-dodecyl-beta-D-maltopyranoside.

13. The method of claim 12, wherein the target tissue is a human pancreatic cancer.

14. The method of claim 9, wherein the targeting ligands are at least one of compounds KB995, KB1005, KB1012, and KB1109.

15. The method of claim 14, wherein the target tissue is a human breast cancer.

16. The method of claim 9, wherein the targeting ligands are at least one of compounds KB1035, KB1036, KB1039, KB1063, KB1064, KB1066, and KB1067.

17. The method of claim 16, wherein the target tissue is a human non-small cell lung carcinoma.

18. The method of claim 9, wherein the targeting ligands are at least one of compounds KB1001, KB1003, KB1042, KB1051, KB1062, KB1096, KB1107, KB1108, and KB1029.

19. The method of claim 18, wherein the target tissue is a human non-small cell lung carcinoma vascular endothelium.

20. The method of claim 9, wherein the targeting ligand is compound KB1061.

21. The method of claim 20, wherein the target tissue is a human pancreatic cancer vascular endothelium.

22. The method of claim 9, wherein the targeting ligand is compound KB1023.

23. The method of claim 22, wherein the anticancer therapeutic agent is a plasmid DNA encoding the antiangiogenic protein human thrombospondin-1 (TSP1).

24. The method of claim 20, wherein the target tissue is a melanoma.

25. The method of claim 9, wherein the targeting ligand is compound is at least one of KB1037, KB1109 and KB1123.

26. A method of isolating a peptidomimetic compound for binding to a target tissue comprising the steps of:
preparing a peptidomimetic library of compositions of formula:
A-scaffold-A', wherein the scaffold is of the formula:

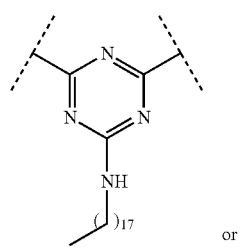

or

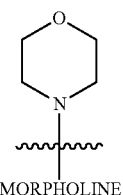
MORPHOLINE contacting a target tissue with the peptidomimetic compounds;
isolating those peptidomimetic compounds that binding specifically to the target tissue; and
characterizing the formula of the composition that bound specifically to the target tissue.

27. The method of claim 26, wherein the method is a high throughput assay and the target tissue includes cells from a patient that are assayed directly following a dissociation step.

28. The method of claim 26, wherein binding of the peptidomimetic library is screened by comparing binding between tumor cells and normal cells.

29. The method of claim 26, wherein the peptidomimetic library is screened directly using time resolved fluorometry.

(a)

(b)

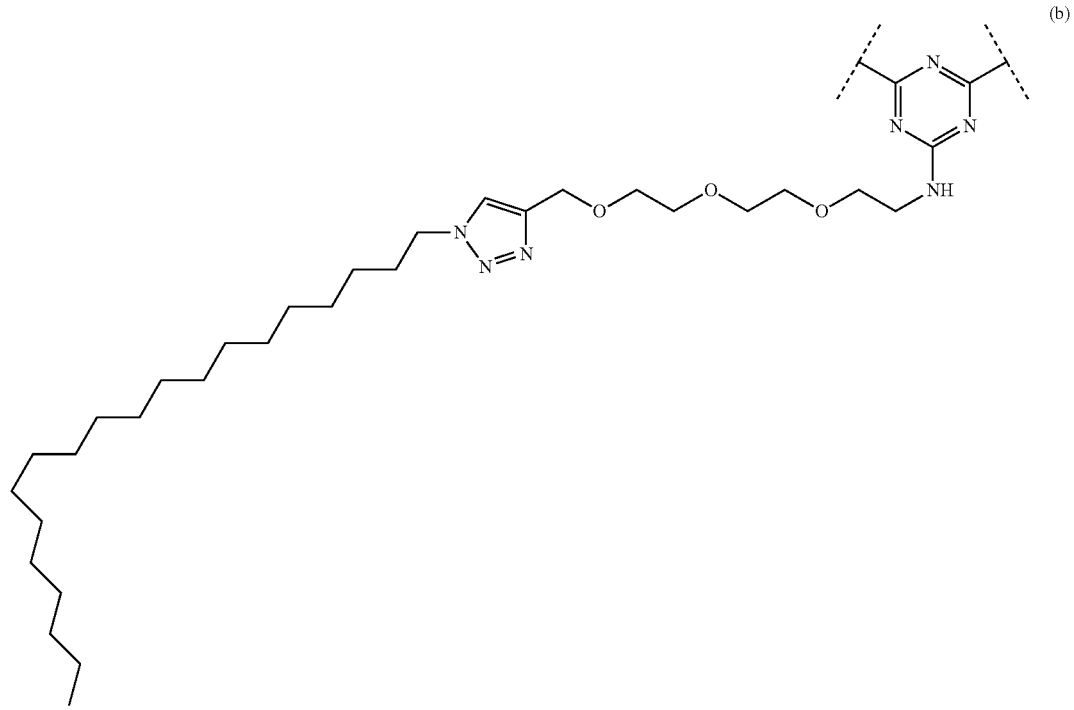

wherein the dotted lines represent the point of attachment to A and A':
wherein A and A' comprise monovalent peptidomimetic compounds, wherein each monovalent peptidomimetic compound has the following formula:

30. The method of claim 26, wherein the peptidomimetic library is screened in a transfection based system.

31. The method of screening for a peptidomimetic compound that binds to a target tissue or cell comprising the steps of:

preparing a peptidomimetic library of compositions of formula:
A-scaffold-A',
wherein the scaffold is of the formula:

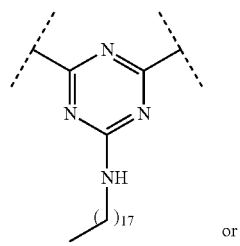

or

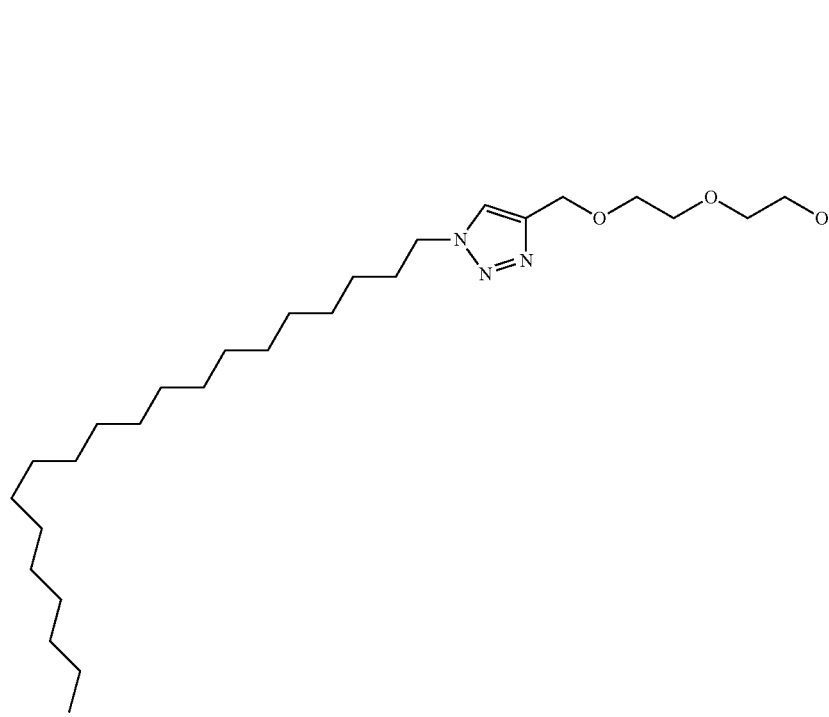

(a)

(b)

wherein the dotted lines represent the point of attachment to A and A':

wherein A and A' comprise peptidomimetic compounds, wherein each monovalent peptidomimetic compound has the following formula:

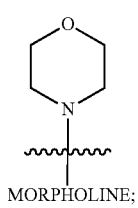

MORPHOLINE;

mixing the peptidomimetic compounds with lipids to form liposomes;

contacting a target tissue with the peptidomimetic compounds;

isolating those peptidomimetic compounds that binding specifically to the target tissue; and characterizing the formula of the composition that bound specifically to the target tissue.

32. A method of screening for a peptidomimetic compound that binds to a target tissue or cell comprising the steps of:

preparing a peptidomimetic library of compositions of formula:
A-scaffold-A',
wherein the scaffold is of the formula:

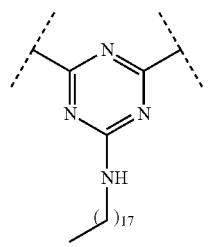

or

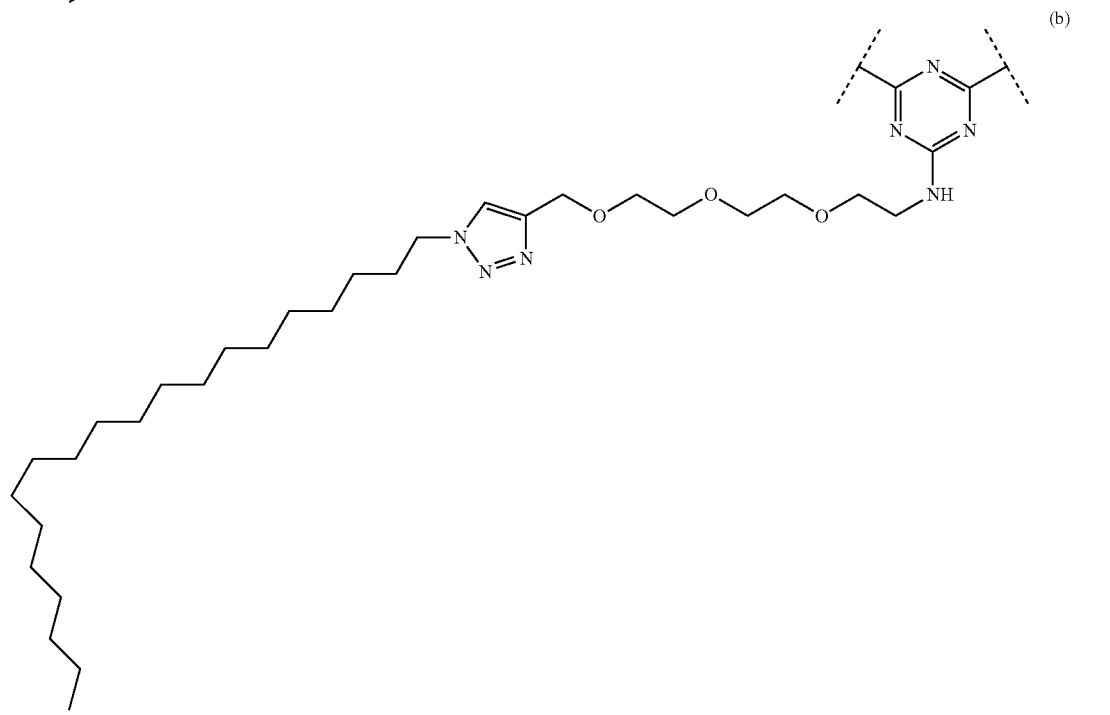

wherein the dotted lines represent the point of attachment to A and A';

wherein A and A' comprise peptidomimetic compounds, wherein each monovalent peptidomimetic compound has the following formula:

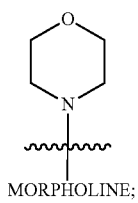

MORPHOLINE;

mixing the peptidomimetic compounds with lipids to form liposomes, wherein the liposomes further comprise a nucleic acid for delivery to a cell;

contacting a target tissue with the peptidomimetic compounds;

isolating those peptidomimetic compounds that binding specifically to the target tissue; and characterizing the formula of the composition that bound specifically to the target tissue.

33. The method of claim 32, wherein the target tissue is defined further as cells in tissue culture.

34. The method of claim 32, wherein the target tissue is defined further as cells in tissue culture and the cells are selected based on the effect of the nucleic acid on the cells.

35. The method of claim 32, wherein the target tissue is defined further as cells in tissue culture, wherein the nucleic acid is a selective marker for negative or positive selection, expresses a selective marker for positive or negative selection, or expresses a detectable marker.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence

```
<220> FEATURE:
<223> OTHER INFORMATION: Synthetic oligonucleotide.

<400> SEQUENCE: 1
tggaattgga ttcgccattt                                              20

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucloetide.

<400> SEQUENCE: 2
tgggtgggtg tgtctacagg a                                            21

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide.

<400> SEQUENCE: 3
ctggaacggt gaaggtgaca                                              20

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 4
aagggacttc ctgtaacaat gca                                          23
```